(12) United States Patent
Moosmann et al.

(10) Patent No.: US 12,370,009 B2
(45) Date of Patent: Jul. 29, 2025

(54) HEAD STABILIZATION DEVICE INTERFACE AND JOINT ASSEMBLY

(71) Applicant: pro med instruments GmbH, Freiburg im Breisgau (DE)

(72) Inventors: Severin Moosmann, Friesenheim (DE); Andreas Blum, Ehrenkirchen (DE); Peter Forst, Emmendingen (DE); Matthias Esser, Freiburg (DE)

(73) Assignee: pro med instruments GmbH, Freiburg im Breisgau (DE)

( * ) Notice: Subject to any disclaimer, the term of this patent is extended or adjusted under 35 U.S.C. 154(b) by 284 days.

(21) Appl. No.: 17/485,692

(22) Filed: Sep. 27, 2021

(65) Prior Publication Data

US 2022/0096195 A1 Mar. 31, 2022

Related U.S. Application Data

(60) Provisional application No. 63/084,101, filed on Sep. 28, 2020.

(51) Int. Cl.
*A61B 90/00* (2016.01)
*A61B 90/14* (2016.01)

(52) U.S. Cl.
CPC .................. *A61B 90/14* (2016.02)

(58) Field of Classification Search
CPC ... A61B 2090/571; A61B 90/25; A61B 90/35; A61B 90/57; A61B 90/14; A61G 13/121; A61G 7/1084; A61G 7/072; A61G 7/0506; A61G 15/125; A61G 13/101–1295; Y10T 403/59; Y10T 403/591; Y10T 403/595; Y10T 403/71; Y10T 403/7117; Y10T 403/7182; Y10T 403/7188; A47C 7/38; A61F 5/3707; A61F 5/37; A61F 5/3769; A61F 5/3792
USPC ........................................................ 128/845
See application file for complete search history.

(56) References Cited

U.S. PATENT DOCUMENTS

| 2,291,782 | A | * | 8/1942 | Allring | E04B 1/6183 403/321 |
| 2,622,831 | A | * | 12/1952 | Fullwood | A61G 13/12 248/292.12 |
| 3,099,441 | A | * | 7/1963 | Ries | A61B 90/14 5/637 |
| 3,572,835 | A | * | 3/1971 | Kees, Jr. | A61G 13/12 5/640 |
| 5,806,933 | A | * | 9/1998 | Tsui | B60N 2/847 297/216.12 |

(Continued)

*Primary Examiner* — Adam Baker
(74) *Attorney, Agent, or Firm* — Frost Brown Todd LLP

(57) ABSTRACT

A joint assembly and adapter couple with a head stabilization device about one or more circumferential toothed rings of the head stabilization device. This coupling provides rotatable adjustment of the head stabilization device about two degrees of freedom including a first longitudinal axis of the head stabilization device and a second longitudinal axis of the joint assembly. The toothed rings of the head stabilization device can have multiple coupling locations to allow for a third degree of freedom for adjustment along the first longitudinal axis. A locking feature is coupled with the adapter to actuate the adapter and joint assembly for selective adjustment of the head stabilization device among the various degrees of freedom for adjustment.

20 Claims, 14 Drawing Sheets

(56) References Cited

U.S. PATENT DOCUMENTS

| | | | | |
|---|---|---|---|---|
| 6,397,414 | B1* | 6/2002 | Lloyd | A61G 13/12 5/643 |
| 9,174,077 | B2* | 11/2015 | Lim | F16L 3/10 |
| 9,216,126 | B2 | 12/2015 | Schuele et al. | |
| 2002/0032927 | A1* | 3/2002 | Dinkler | A61G 13/12 5/601 |
| 2004/0055089 | A1* | 3/2004 | Dinkler | A61B 90/14 5/601 |
| 2006/0255220 | A1* | 11/2006 | Skripps | A61G 13/04 248/228.4 |
| 2008/0078031 | A1* | 4/2008 | Weinstein | A61G 13/12 359/865 |
| 2009/0124861 | A1* | 5/2009 | Fetzer | A61B 90/50 600/226 |
| 2014/0059771 | A1* | 3/2014 | Schuele | A61B 90/14 5/622 |
| 2021/0236321 | A1 | 8/2021 | Forst et al. | |

* cited by examiner

HEAD STABILIZATION DEVICE INTERFACE AND JOINT ASSEMBLY

PRIORITY

This application claims priority to U.S. Provisional Patent Application Ser. No. 63/084,101, filed Sep. 28, 2020 entitled "HEAD STABILIZATION DEVICE INTERFACE AND JOINT ASSEMBLY," the disclosure of which is incorporated by reference herein.

BACKGROUND

During certain medical procedures it may be necessary or desirable to stabilize all or a portion of a patient such that the patient or portion of the patient is immobilized. In certain neurological procedures the portion stabilized may include the head and/or neck of the patient. In such procedures, a patient can be positioned on a table or board structure (e.g., surgical table, OR table, transport table, transfer board, etc.). Certain head fixation or stabilization devices (sometimes herein referred to as "HFDs" or "HFD" in singular) and methods may be used to stabilize a certain portion of the patient. For example, a skull clamp is a type of head stabilization device that may be used to stabilize the head and/or neck of the patient. When using a HFD, such as a skull clamp for instance, the device may be selectively connected with other structures to effectively position and stabilize the patient.

While a variety of head stabilization systems and method of use of the same have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements.

Figure 1:
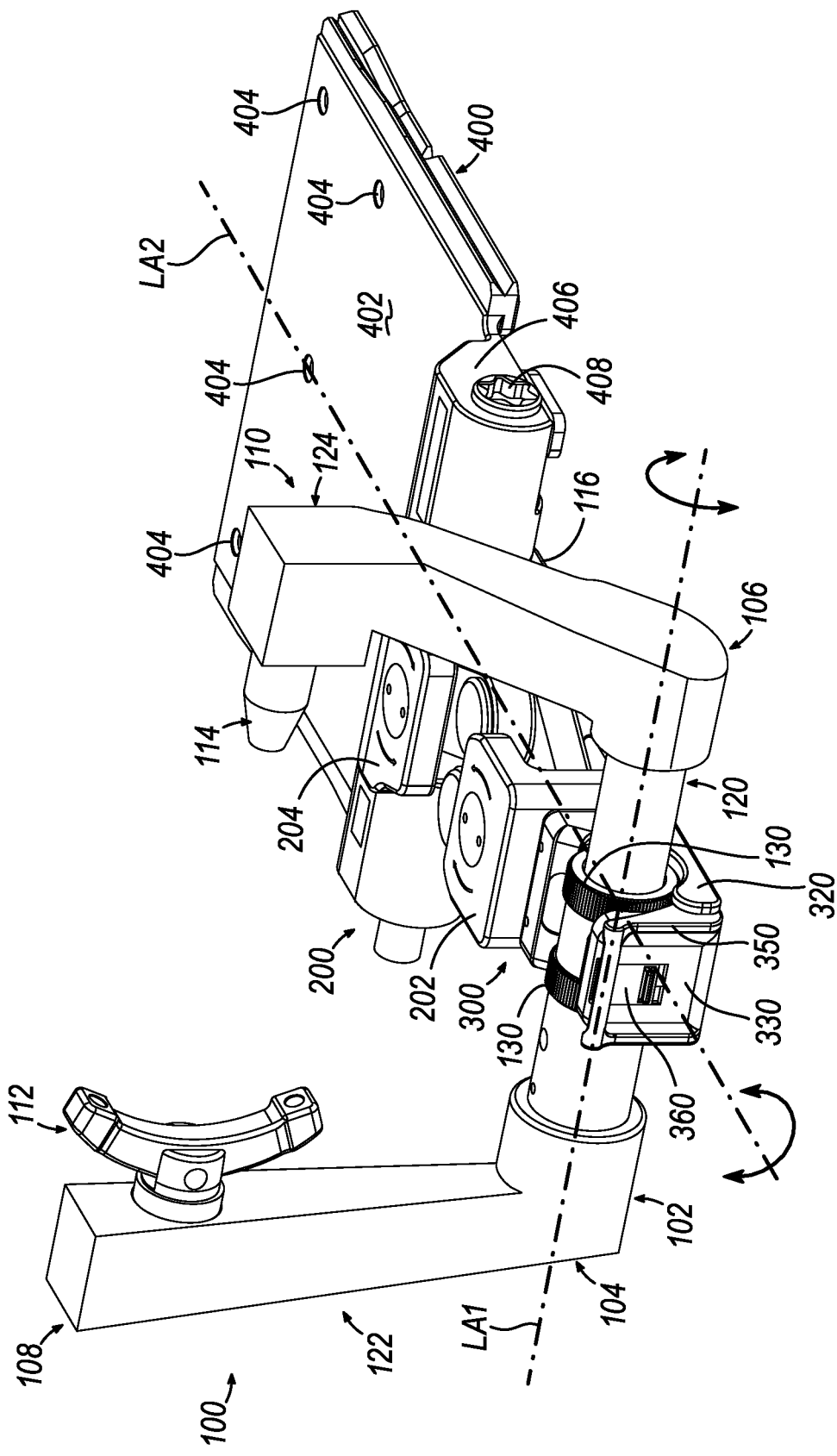
FIG. 1 depicts a perspective view of an exemplary head stabilization system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

FIG. 1 illustrates an exemplary head stabilization system (10) that can be used to stabilize a patient's head for a medical procedure. System (10) comprises a joint assembly (200) and an adapter (300) coupling a head stabilization device (100) with a table adapter (400). Throughout the specification the term "head stabilization device" is used interchangeably with the terms "head fixation device," or "skull clamp." In the illustrated versions here head stabilization device (100) has the shape or form of a skull clamp. Skull clamp (100) defines a first longitudinal axis (LA1). Joint assembly (200) defines a second longitudinal axis (LA2) that is transverse to the first longitudinal axis (LA1). Adapter (300) is translatable and rotatable relative to joint assembly (200), as will be discussed in more detail below. Skull clamp (100) is coupled with adapter (300) which is coupled with joint assembly (200) such that skull clamp (100) is rotatably adjustable in at least two directions to position head stabilization device (100) relative to table adapter (400). For instance, skull clamp (100) is rotatable about the first longitudinal axis (LA1) of skull clamp (100) and about the second longitudinal axis (LA2) of joint assembly (200).

Adapter (300) is configured to move between an open state and a closed state. In the open state, adapter (300) is spaced a first distance away from joint assembly (200) to allow rotation of skull clamp (100) about the first and second longitudinal axes (LA1, LA2). In the closed state, adapter (300) is spaced a second distance away from joint assembly (200) that is less than the first distance to inhibit rotation of skull clamp (100) about the first and second longitudinal axes (LA1, LA2). A locking feature can be used to actuate adapter (300) between the open and closed states. Additional components and operability of system (10) is discussed in more detail below.

I. Exemplary Skull Clamp

FIG. 1 illustrates an exemplary skull clamp (100) comprising a frame (102) having a first frame portion (104) and a second frame portion (106). In the illustrated version, frame portions (104, 106) are assembled together such that skull clamp (100) includes a base defining a generally lateral portion (120), and a pair of generally upright portions (122, 124). Generally lateral portion (120) is configured to be received within adapter (300) and defines longitudinal axis (LA1). Lateral portion (120) comprises at least one set of engaging features or engaging members that in the illustrated example are shown as a plurality of teeth (130) positioned about a circumference of lateral portion (120). In some instances, teeth (130) may be referred to as radial or oriented radially about lateral portion (120). In some instances, teeth (130) may be referred to as circumferentially positioned or oriented about lateral portion (120). In the illustrated version, lateral portion (120) includes two sets of teeth (130), but any other suitable number can be used. Also, while in the present example, teeth (130) extend continuously entirely around the circumference of lateral portion (120), in other versions teeth (130) may extend discontinuously entirely or only partially around the circumference of lateral portion (120). In some instances, teeth on the lateral portion may be referred to as defining a gear or gear ring.

Frame portions (104, 106) are adjustably connectable to adjust a spacing between them. This movement alters the length of lateral portion (120), which in the present example includes two telescoping components or portions. Frame portions (104, 106) include respective receiving portions (108, 110) that are each configured to receive a stabilization assembly (112, 114). In the illustrated version, stabilization assembly (112) comprises a rocker arm design with two pins while stabilization assembly (114) comprises a single pin. Further examples of head stabilization devices and related concepts are disclosed in U.S. Patent Pub. No. 2021/0236321, entitled "Head Stabilization Device Tensioning Feature and Method of Use," published Aug. 5, 2021, the disclosure of which is incorporated by reference herein.

II. Exemplary Adapters and Joint Assembly

Figure 2:
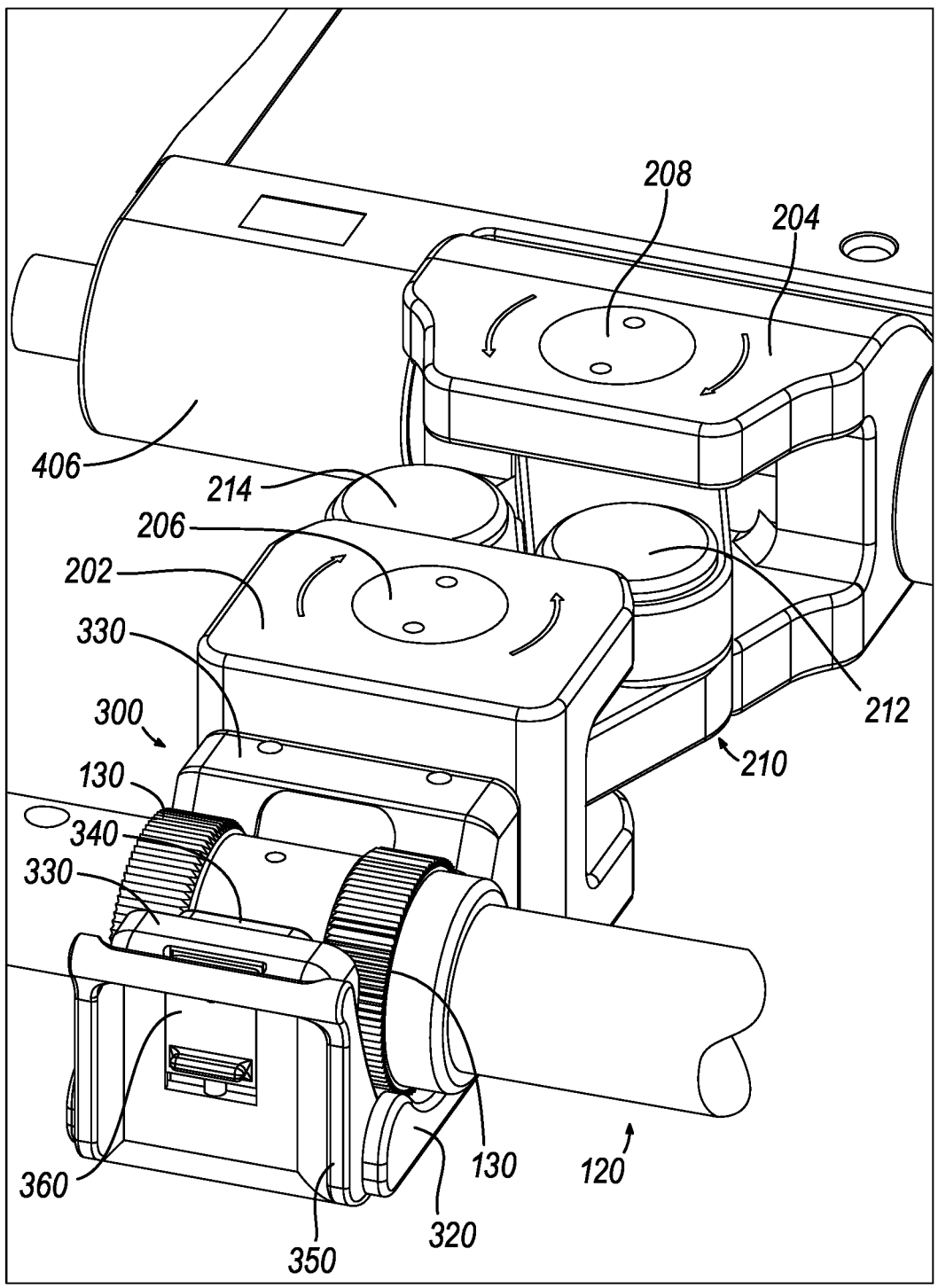
FIG. 2 depicts an enlarged perspective view of a joint assembly and an adapter coupling a skull clamp with a table adapter of the head stabilization system of FIG. 1.

FIGS. 1 and 2 show an exemplary table adapter (400), joint assembly (200), and adapter (300). Table adapter (400) can be directly or indirectly coupled with a table or board structure for supporting a patient. For instance, table adapter (400) comprises a body (402) having one or more bores (404) configured to receive fasteners (not shown) to connect table adapter (400) with the table or board structure. A proximal end portion (406) of table adapter (400) defines an opening having a shaft (408) inserted therethrough. In the illustrated version, shaft (408) is coupled with joint assembly (200) such that joint assembly (200) is rotatable relative to table adapter (400) about shaft (408).

As shown in the illustrated version of FIGS. 1 and 2, joint assembly (200) comprises a proximal joint (202) that connects with adapter (300), which is configured to connect with skull clamp (100). At its distal end, joint assembly (200) comprises a distal joint (204), which is configured to connect with table adapter (400) via shaft (408). Joint assembly (200) includes actuators (206, 208) extending through proximal joint (202) and distal joint (204) respectively. Actuators (206, 208) further extend through a central joint (210). Central joint (210) is configured as a parallelogram member in the illustrated version. Actuators (206, 208) control the adjustability of central joint (210) by selectively moving central joint (210) relative to the attached proximal joint (202) and distal joint (204).

For instance, joint assembly (200) can be adjusted to a fully retracted position with central joint (210) in a collapsed configuration such that the distance between proximal joint (202) and distal joint (204) is at a minimum. Joint assembly (200) can be adjusted to a fully extended position with central joint (210) in an extended configuration such that the distance between proximal joint (202) and distal joint (204) is at a maximum. Joint assembly (200) can also be adjusted side to side or in a lateral adjustment by rotating central joint (210) about the axis defined by bolt (212) and/or bolt (214). Further examples of adapters, joint assemblies, and related concepts are disclosed in U.S. Pat. No. 9,216,126, entitled "Table Adapter with Joint Assembly," issued Dec. 22, 2015, the disclosure of which is incorporated by reference herein.

Figure 3A:
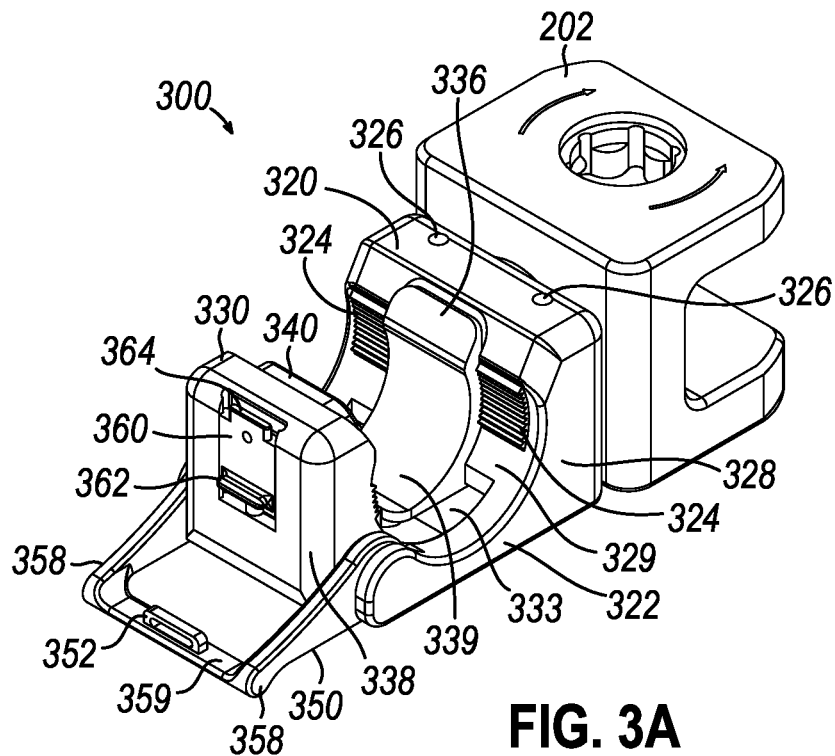
FIG. 3A depicts a perspective view of a proximal portion of the joint assembly and the adapter of FIG. 2 with the skull clamp removed and with the adapter in an open state.
Figure 3B:
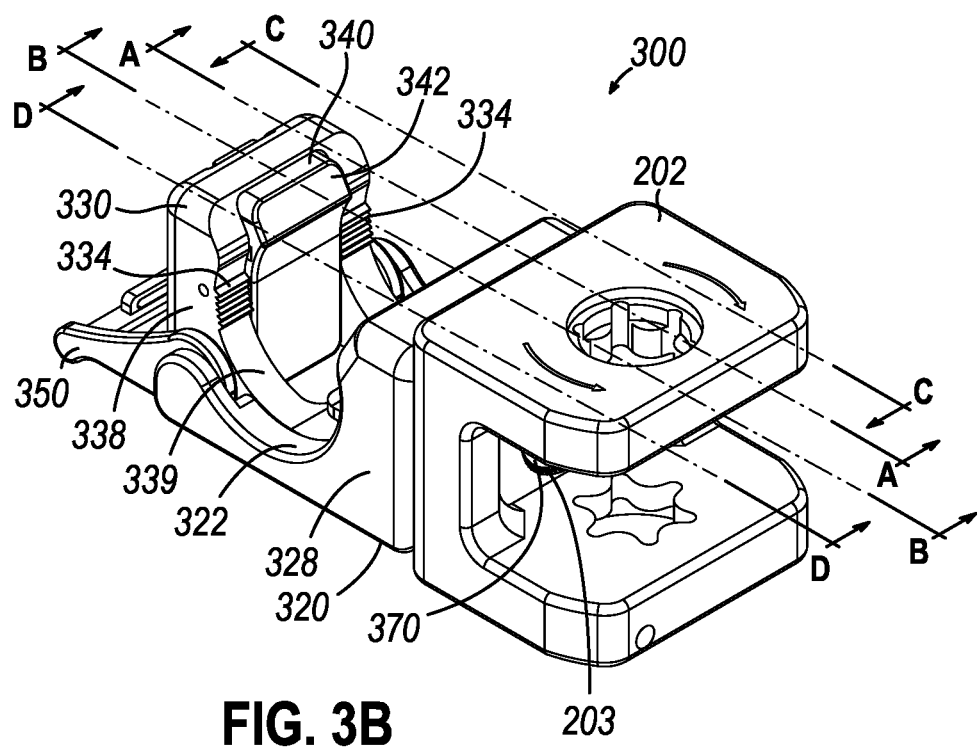
FIG. 3B depicts another perspective view of the proximal portion of the joint assembly and the adapter of FIG. 2 with the skull clamp removed and with the adapter in an open state.

Referring now to FIGS. 3A and 3B, adapter (300) comprises an attachment support (320), and a slide support (330). Attachment support (320) comprises a body (328)

having a pair of arms (322) extending proximally from each lower side portion of body (328). Arms (322) are sufficiently spaced apart to slidingly receive slide support (330) between arms (322). Body (328) of attachment support (320) further comprises an arcuate interior surface (329) having a set of engaging members or engaging features illustrated as a plurality of teeth (324) on each upper side portion of arcuate interior surface (329). While two sets of teeth (324) are shown in the illustrated version, any other suitable number of sets of teeth (324) can be used. Attachment support (320) is rotatably coupled to proximal joint (202) by pins (326), as will be discussed in more detail below. A locking shaft (370) is positioned through attachment support (320) and proximal joint (202) such that locking shaft (370) is translatable relative to attachment support (320) and proximal joint (202) to thereby selectively maintain or adjust the rotatable position of attachment support (320) relative to proximal joint (202).

Slide support (330) comprises a body (338) comprising an arcuate interior surface (339) that is sized to correspond to lateral portion (120) of skull clamp (100). A set of engaging members or engaging features illustrated as a plurality of teeth (334) are positioned on each upper side portion of arcuate interior surface (339), opposite of teeth (324) of attachment support (320). While two sets of teeth (334) are shown in the illustrated version, any other suitable number of sets of teeth (334) can be used. Slide support (330) further comprises a pair of flanges (333) extending outwardly from each exterior side portion of slide support (330) such that flanges (333) are each slidingly received within an arm (322) of attachment support (320) to allow slide support (330) to translate relative to attachment support (320), as will be discussed in more detail below. A snap element (340) is positioned within interior surface (339) of slide support (330), between each set of teeth (334), such that snap element (340) is translatable relative to interior surface (339) of slide support (330). Snap element (340) includes a beveled surface (342) on an upper interior surface of snap element (340). While the illustrated version shows snap element (340) as translating relative to slide support (330), in some other versions, snap element (340) is rotatable or pivotable. Slide support (330) includes a corresponding beveled surface (336) on an opposing upper interior surface (339) of slide support (330).

A locking lever (350) comprising a lever (359) and a pair of arms (358) extending outwardly from lever (359) is coupled with slide support (330) such that an arm (358) of locking lever (350) is positioned between each arm (322) of attachment support (320) and body (338) of slide support (330). Accordingly, locking lever (350) is pivotable relative to slide support (330) such that locking lever (350) is configured to translate slide support (330) relative to attachment support (320). A locking bar (360) is positioned on body (338) of slide support (330) such that locking bar (360) is translatable along body (338). Locking bar (360) comprises a flange (362) configured to be gripped by a user to thereby translate locking bar (360) relative to slide support (330). Locking bar (360) further comprises a tab (364) extending upwardly from locking bar (360) that is configured to be inserted within a channel (352) of locking lever (350). Still other suitable configurations for joint assembly (200), adapter (300), and table adapter (400) will be apparent to one with ordinary skill in the art in view of the teachings herein.

III. Exemplary Method and Operability of Adapter and Joint Assembly

Figure 4A:
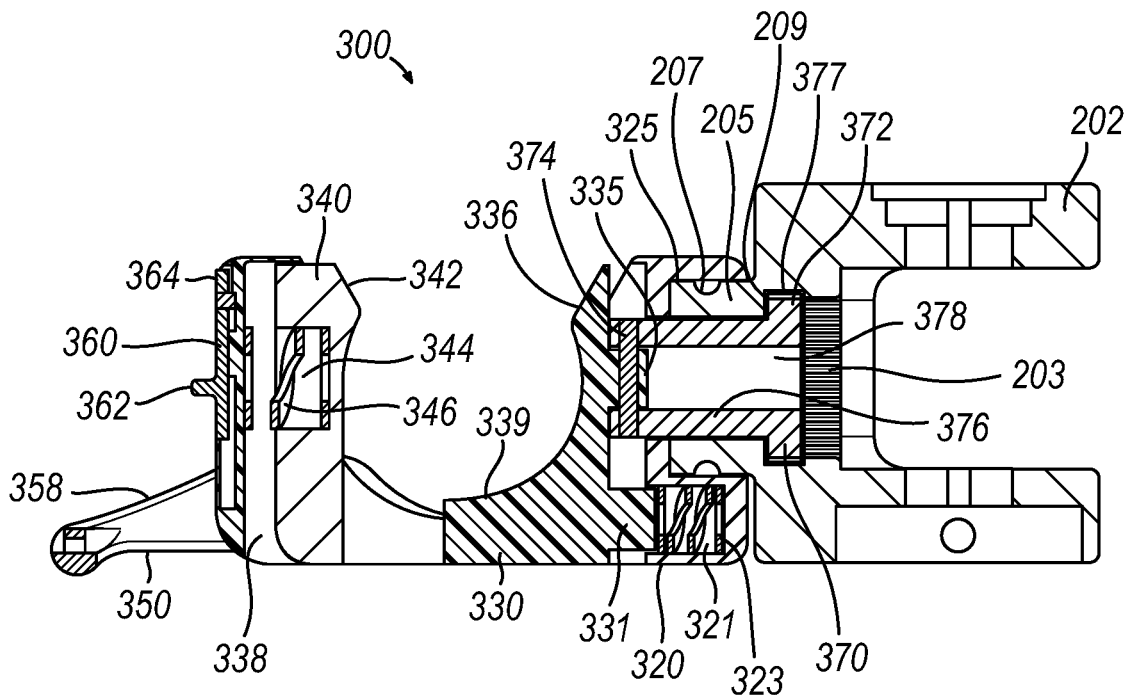
FIG. 4A depicts a first series view in cross section taken along line A-A of FIG. 3B, showing the adapter in an open state.
Figure 4B:
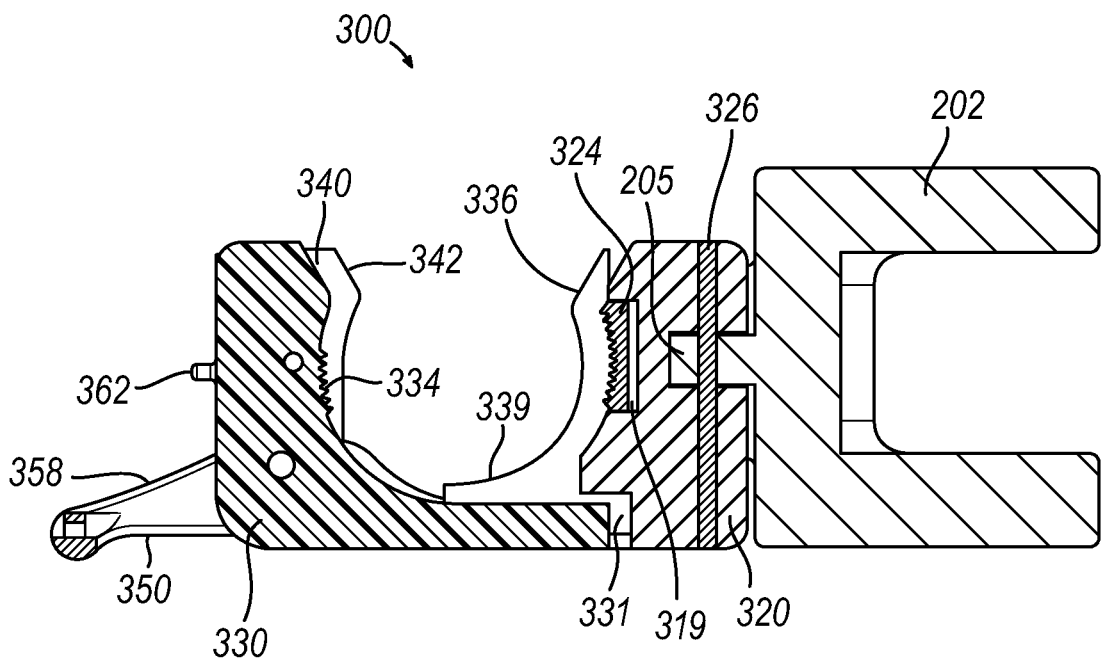
FIG. 4B depicts a first series view in cross section taken along line B-B of FIG. 3B—the cross-section along line C-C being a mirror image—showing the adapter in an open state.

Adapter (300) is configured to be moved between an open state and a closed state. For instance, FIGS. 4A and 4B show adapter (300) in the open state, with skull clamp (100) removed from adapter (300). In the open state, locking bar (360) is positioned downward within slide support (330) such that tab (364) is removed from channel (352) of locking lever (350). Locking lever (350) is pivoted downward relative to slide support (350) such that slide support (330) is translated away from attachment support (320). As best seen in FIG. 4A, attachment support (320) includes a first resilient member (323) positioned within a channel (321) of attachment support (320) that is positioned against a flange (331) of slide support (330) positioned within channel (321). First resilient member (323) thereby resiliently biases slide support (330) away from attachment support (320). In this position, interior surface (339) of slide support (330) is positioned proximally relative to teeth (324) of attachment support (320), as shown in FIG. 4B. In some versions, an elastomeric bumper (319) is inserted between teeth (324) and attachment support (320). Bumper (319) is slightly compressible to compensate for any variability due to manufacturing tolerances when fabricating components of adapter (300) and skull clamp (100) such that completely engagement between teeth (130) of skull clamp (100) and teeth (324, 334) of adapter (300) is achieved during use. In some other versions, the bumper can be additionally or alternatively positioned between teeth (324) and slide support (330).

Referring again to FIGS. 4A and 4B, snap element (340) includes a second resilient member (346) positioned within a channel (344) of snap element (340) such that second resilient member (346) is positioned against slide support (330). Second resilient member (323) thereby resiliently biases snap element (340) away distally from slide support (330). In this position, snap element (340) is positioned distally relative to teeth (334) of slide support (330).

A distal end of attachment support (320) includes a recess (325) configured to receive a flange (205) of proximal joint (202) that extends proximally from proximal joint (202). Flange (205) of proximal joint (202) includes an annular recess (207) extending within a circumference of flange (205). Referring to FIG. 4B, a pin (326) is inserted through each distal side portion of attachment support (320) such that each pin (326) is inserted within recess of attachment support (320) and recess (207) of proximal joint (202). This allows pins (326) and attachment support (320) to rotate relative to proximal joint (202).

Referring back to FIG. 4A, locking shaft (370) is positioned through a bore of flange (205) of proximal joint (202). Locking shaft (370) comprises a generally cylindrical body (376) having an annular flange (372) extending outward from a distal end portion of body (376). In the illustrated version, flange (372) includes engaging features or engaging members illustrated as teeth (377) positioned about a circumference of flange (372) that are configured to engage with engaging members or engaging features illustrated as teeth (203) of proximal joint (202). In the open state, locking shaft is positioned proximally relative to teeth (203) within a channel (209) of proximal joint (202). Body (376) of locking shaft (272) further includes an opening (378) extending longitudinally therethrough that is sized to receive a protrusion (335) of slide support (330) within opening (378). A proximal end portion of body (376) and protrusion (335) each define an opening extending laterally therethrough to receive a pin (374). Pin (374) thereby couples protrusion (335) of slide support (330) with body (376) of locking shaft (372) to maintain the position of locking shaft (372) relative to slide support (330). Accordingly, locking shaft (370) is configured to translate simultaneously with slide support (330).

Figure 5A:
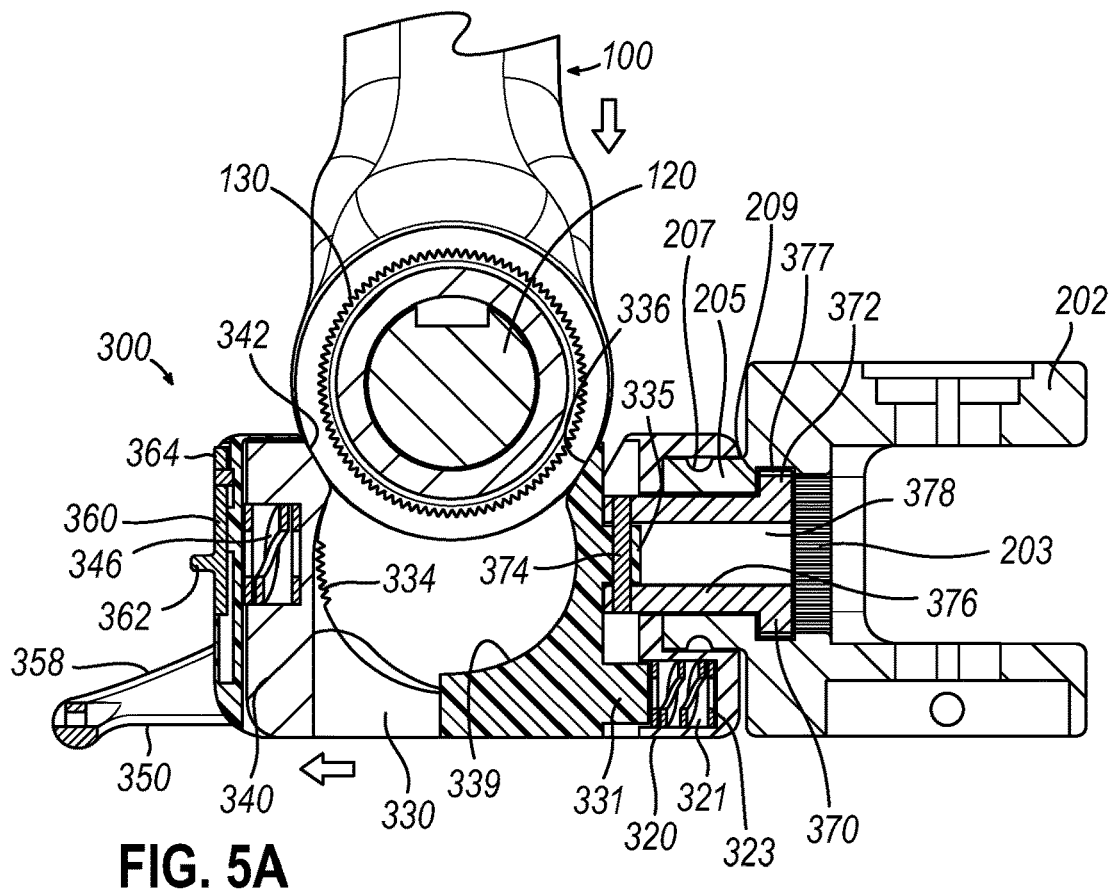
FIG. 5A depicts a second series view in cross section taken along line A-A of FIG. 3B, showing the adapter in an open state with the skull clamp partially received within the adapter.
Figure 5B:
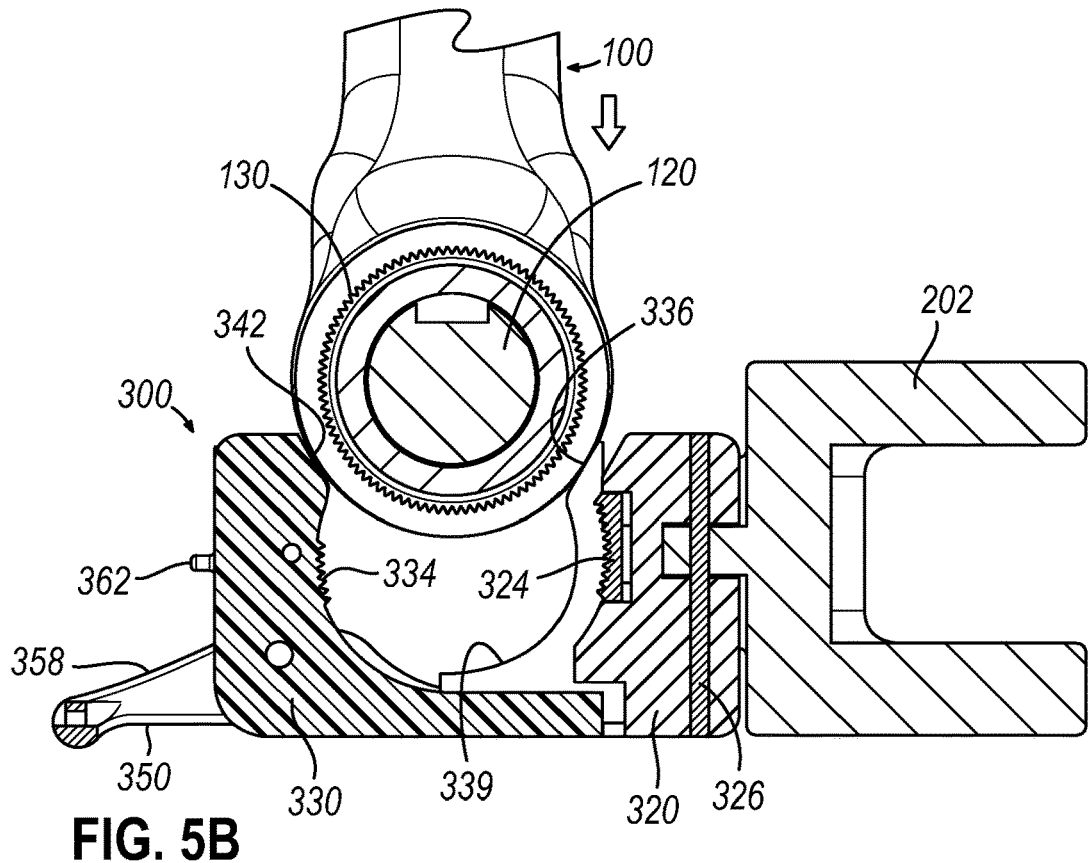
FIG. 5B depicts a second series view in cross section taken along line B-B of FIG. 3B—the cross-section along line C-C being a mirror image—showing the adapter in an open state with the skull clamp partially received within the adapter.

FIGS. 5A and 5B illustrate adapter (300) in the open state with skull clamp (100) partially received within adapter (300). As shown, lateral portion (120) of skull clamp (100) engages beveled surfaces (342, 336) of snap element (340) and slide support (330) as lateral portion (120) is inserted within adapter (300). Downward force causes lateral portion (120) to translate snap element (340) proximally relative to slide support (330) to compress resilient member (346). This allows lateral portion (120) to slide within slide support (330) via a snap fit as will be described further below.

Figure 6A:
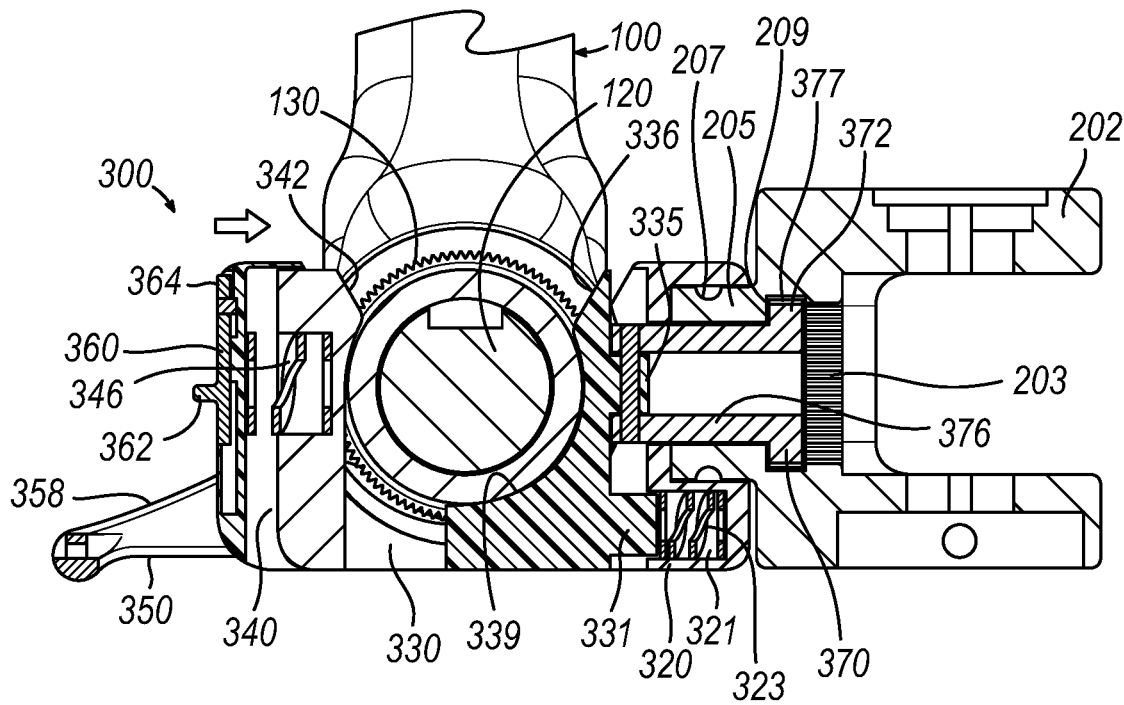
FIG. 6A depicts a third series view in cross section taken along line A-A of FIG. 3B, showing the adapter in an open state with the skull clamp fully received within the adapter.
Figure 6B:
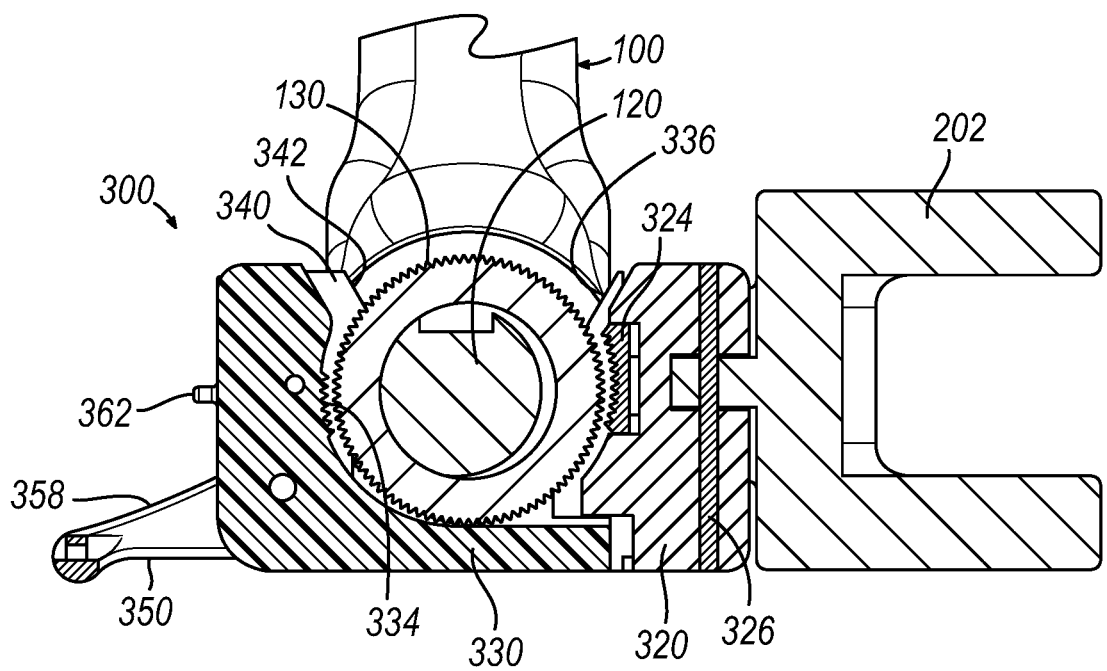
FIG. 6B depicts a third series view in cross section taken along line B-B or line C-C of FIG. 3B, showing the adapter in an open state with the skull clamp fully received within the adapter.

FIGS. 6A and 6B illustrate adapter (300) in the open state with skull clamp (100) fully received within adapter (300). As shown, lateral portion (120) of skull clamp (100) has been moved downward further compared to FIGS. 5A and 5B such that lateral portion (120) is fully received within a arcuate space or void defined by interior surfaces of slide support (330), attachment support (320), and snap element (340). With lateral portion (120) fully received within adapter (300), resilient member (346) translates snap element (340) distally relative to slide support (330) to return snap element (340) to be positioned distally relative to teeth (334) of slide support (330) and engage skull clamp (100). In this manner, snap element (340) contacts or engages with a smooth surface of lateral portion (120) located between rings of teeth (130) as best seen in FIG. 6A. Snap element (340) thereby maintains the position of skull clamp (100) within adapter (300). However, with locking lever (350) in the unlocked or open stat, slide support (330) is spaced sufficiently away from attachment support (320) such that teeth (334) of slide support (330) and teeth (326) of attachment support (320) do not engage teeth (130) of lateral portion (120) of skull clamp (100). This allows skull clamp (100) to be rotated relative to supports (320, 330) of adapter (300) about the longitudinal axis (LA1) of skull clamp (100). With adapter (300) in the open state, skull clamp (100) may further be rotated with supports (320, 330) relative to proximal joint (202) about the longitudinal axis (LA2) of joint assembly (200).

Figure 7A:
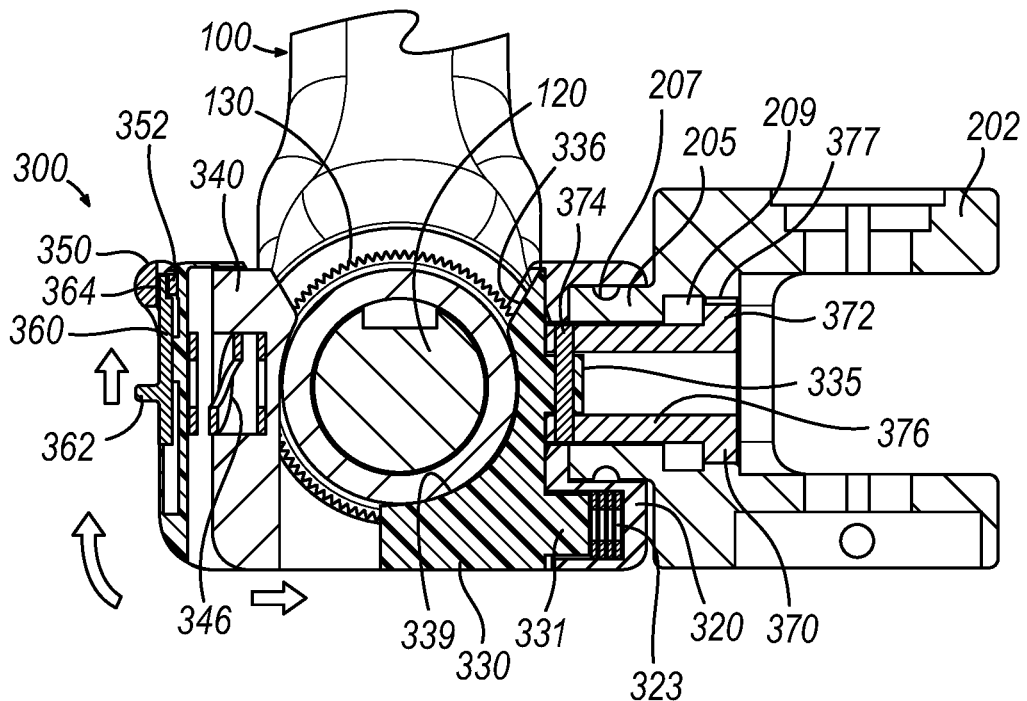
FIG. 7A depicts a fourth series view in cross section taken along line A-A of FIG. 3B, showing the adapter in a closed and locked state with the skull clamp secured within the adapter.
Figure 7B:
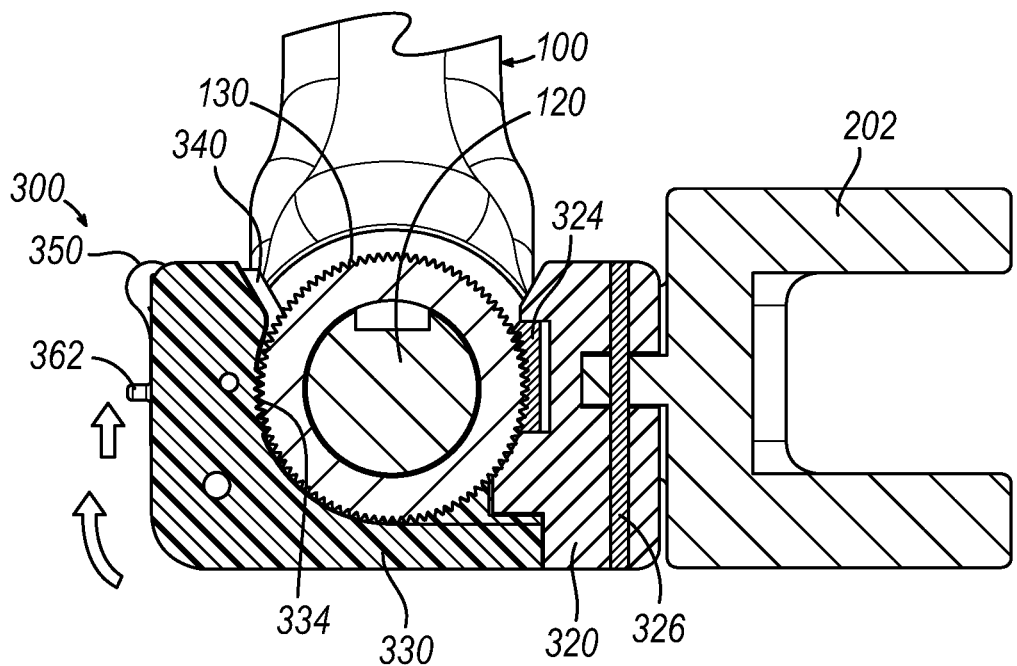
FIG. 7B depicts a fourth series view in cross section taken along line B-B of FIG. 3B—the cross-section along line C-C being a mirror image—showing the adapter in a closed and locked state with the skull clamp secured within the adapter.
Figure 8:
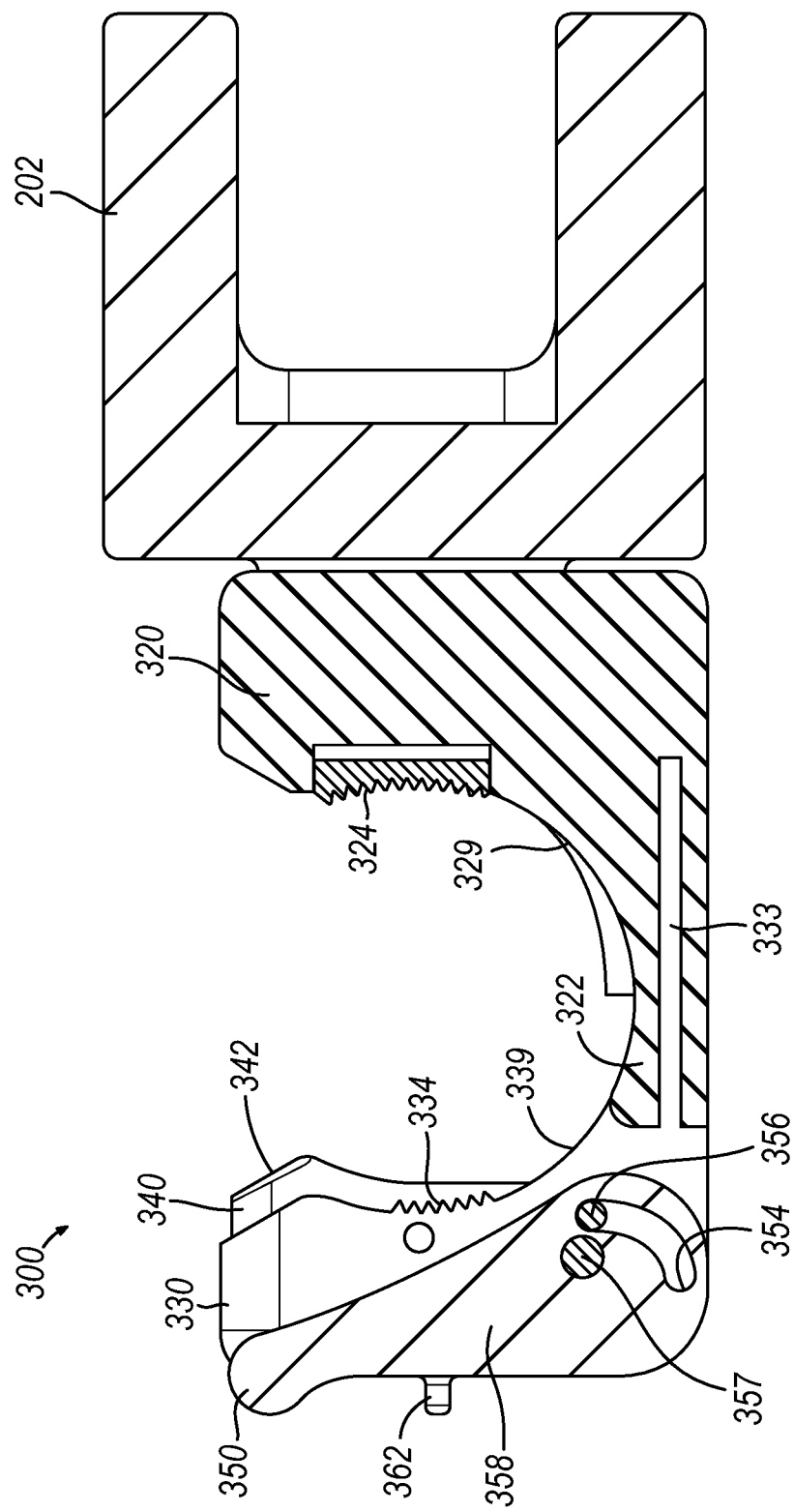
FIG. 8 depicts a cross section view taken along line D-D of FIG. 3B, showing the adapter in a closed and locked state.

Once skull clamp (100) is adjusted about a select one or both of the longitudinal axes (LA1, LA2), adapter (300) can be moved from the open state to the closed state. FIGS. 7A and 7B show adapter (300) in the closed state to thereby maintain the position of skull clamp (100) relative to adapter (300). For instance, locking lever (350) is pivoted upward relative to slide support (330). Referring to FIG. 8, locking lever (350) includes an arcuate opening (354) extending through each arm (358) of locking lever (350). A pin or post (356) of attachment support (320) is inserted through arcuate opening (354), and each arm (358) also has a pinned connection with slide support (330) via pin or post (357) such that as locking lever (350) is pivoted upward, locking lever (350) translates slide support (330) distally toward attachment support (320).

Referring to FIGS. 7A and 7B, slide support (330) is thereby translated within attachment support (320) to compress resilient member (323). The translation of slide support (320) further causes teeth (334) of slide support (330) and teeth (324) of attachment support (320) to engage teeth (130) of skull clamp (100). This maintains or secures the rotational position of skull clamp (100) about longitudinal axis (LA1) relative to adapter (300). The translation of slide support (330) also simultaneously translates locking shaft (370) within proximal joint (202). For instance, annular flange (372) of locking shaft (370) is translated from within channel (209) of proximal joint (202) to engage teeth (203) of proximal joint (202). Locking shaft (370) thereby locks the rotational movement of attachment support (320) about longitudinal axis (LA2) relative to proximal joint (202). In the illustrated version, with adapter (300) in the closed state, locking bar (360) is translated upward relative to slide support (330) to insert tab (364) of locking bar (360) within channel (352) of locking lever (350). Locking bar (360) thereby locks the position of locking lever (350) relative to slide support (330). Accordingly, adapter (300) is in a closed and locked state.

Skull clamp (100) can also be selectively readjusted and/or removed from adapter (300). For instance, locking bar (360) can be translated downward to remove tab (362) of locking bar (360) from channel (352) of locking lever (350). Locking lever (350) can be pivoted downward relative to slide support (330) to return adapter (300) to the open state, as shown in FIGS. 6A and 6B. In the open state, slide support (330) is translated proximally by resilient member (323) to thereby disengage teeth (334) of slide support (330) and teeth (324) of attachment support (320) from teeth (130) of skull clamp (100). The translation of slide support (330) further translates locking shaft (370) proximally to disengage the teeth of locking shaft (370) from teeth (203) of proximal joint (202). Skull clamp (100) is thereby able to be rotated about the longitudinally axes (LA1, LA2) such that skull clamp (100) can be repositioned or readjusted. As shown and described above, the system of joint assembly (200) and adapter (300) with skull clamp (100) provides for an interface that allows for the ability to make positional adjustments about two degrees of freedom at the same time. In other words, the two degrees of freedom—coinciding to rotational adjustments about longitudinal axes (LA1, LA2)—remain adjustable at the same time so that adjustments can be made to either or both before either or both are secured or moved to their non-adjustable state.

Additionally, or alternatively, skull clamp (100) can be removed from adapter (300). For instance, skull clamp (100) can be pulled upward relative to adapter (300) to thereby remove skull clamp (100) from adapter (300), as shown in FIGS. 5A and 5B. With adapter (300) in the unlocked state, as skull clamp (100) is translated upward, skull clamp (100) engages snap element (340) to drive snap element (340) proximally within slide support (330). Skull clamp (100) is thereby releasable or removable from adapter (300), and snap element (340) can return to the distal position, as shown in FIGS. 4A and 4B. Other suitable methods for operating joint assembly (200) and adapter (300) will be apparent to one with ordinary skill in the art in view of the teachings herein.

IV. Exemplary Skull Clamp with Central and Outer Sets of Teeth

Figure 9:
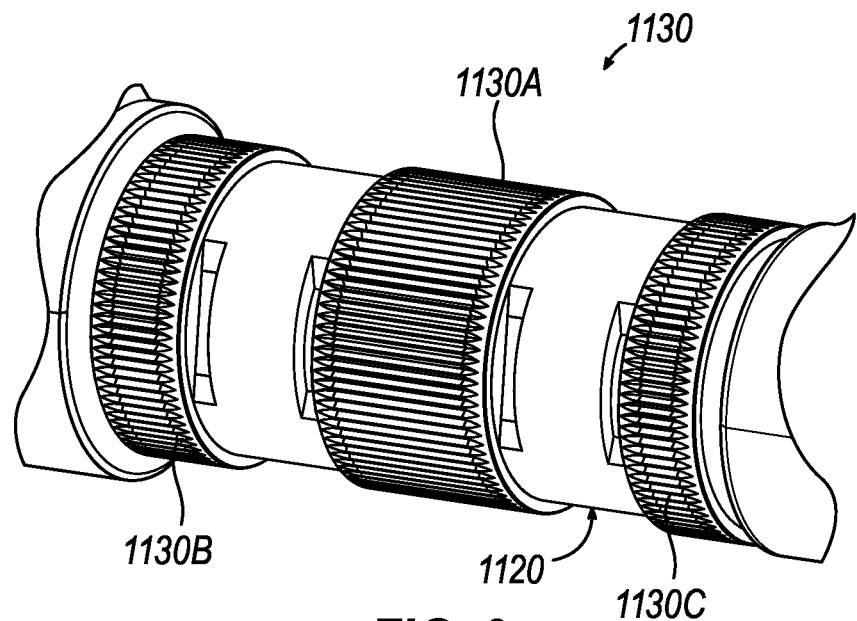
FIG. 9 depicts a perspective view of a portion of another lateral portion of the skull clamp having an alternate configuration for the circumferentially positioned plurality of teeth.

FIG. 9 depicts another lateral portion (1120) usable with head stabilization system (10) and skull clamp (100) that has three sets of teeth (1130) similar to teeth (130). For instance, lateral portion (1120) may replace lateral portion (120). With lateral portion (1120), there is a middle or central set of teeth (1130A) and two sets of outer teeth (1130B, 1130C) with one on each side of central set of teeth (1130A). With this configuration, multiple adapters, such as adapter (300) or other similar adapters, can be coupled with lateral portion (1120) and thus skull clamp (100). For instance, central set of teeth (1130A) are broader or wider in the present example and thus can accommodate portions of more than one adapter, such as adapter (300). At the same time, each of outer teeth (1130B, 1130C) engage one of the respective multiple adapters. In an example using two adapters (300) with lateral portion (1120), one of adapters (3000) will engage with teeth (1130A, 1130B) while the other of adapters (300) will engage with teeth (1130A, 1130C). It should be noted that in some other versions of lateral portion (1120) central teeth (1130A) can be split into distinct toothed rings as opposed to being joined or merged as into a single toothed ring configuration as shown in the present illustrated version.

In another example of lateral portion (1120) used with skull clamp (100) in place of lateral portion (120), a single adapter (300) can be coupled with teeth (1130). In such an example, the interface defined by teeth (1130)—comprising teeth (1130A, 1130B, 1130C)—provides another degree of freedom for adjustments. This additional degree of freedom for adjustment is lateral adjustment along longitudinal axis (LA1) because adapter (300), when in the open state, can now be moved laterally along lateral portion (1120). In other words, lateral portion (1120) of the skull clamp provides multiple locations at which adapter (300) can be coupled with lateral portion (1120). It should be noted that this additional degree of freedom is in combination with the other adjustment degrees of freedom mentioned above—rotation about longitudinal axes (LA1, LA2). In this manner then, skull clamp (100) with lateral portion (1120), when used with adapter (300) and joint assembly (200) provides for three adjustment degrees of freedom that may be adjusted at the same time based on a single actuator associated with adapter (300).

In view of the teachings herein, other ways to configure teeth (1130) of lateral portion (1120) will be apparent to those of ordinary skill in the art to allow for coupling multiple adapters and/or for providing an additional lateral adjustment degree of freedom along longitudinal axis (LA1). By way of example only and not limitation, a lateral portion could be configured with a single continuous ring of teeth that extends substantially along the length of the lateral portion to allow for either or both of multiple adapter coupling and/or lateral adjustment as mentioned. Still in another example similar to lateral portion (120) described above, teeth (130) may be configured with a greater width such that teeth (130) extend along the length of lateral portion (120) to a greater amount to provide for more coupling locations with one or more adapters (300).

Figure 10:
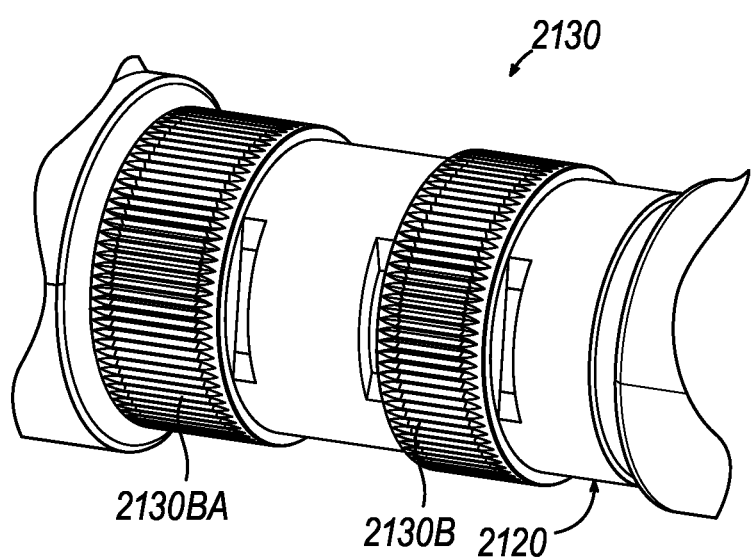
FIG. 10 depicts a perspective view of a portion of another lateral portion of the skull clamp having an alternate configuration for the circumferentially positioned plurality of teeth.

V. Exemplary Skull Clamp with Multiple Sets of Teeth Configured for Engagement with Multiple Adapters FIG. 10 depicts another lateral portion (2120) usable with skull clamp (100) and head stabilization system (10). For instance, lateral portion (2120) may replace lateral portion (120). Lateral portion (2120) teeth (2130) that comprise two sets of teeth (2130A, 2130B) with each set of teeth (2130A, 2130B) configured for selective engagement with an adapter, such as adapter (300) or a similar adapter. In one example, a single adapter may be used with lateral portion (2120) where the adapter is configured like adapter (300) with spaced apart teeth (324, 334) that would engage teeth (2130A, 2130B) of lateral portion (2120). In still another example, multiple adapters may be used with lateral portion (2120). Where multiple adapters are used, the adapters are configured with one central gear ring or teeth section that would engage with one of teeth rings (2130A, 2130B) such that lateral portion (2120) can accommodate multiple adapters.

Where multiple adapters are used, it should be noted all adapters are not required to couple with joint assembly (200) and table adapter (400). For instance, the adapter can be modified or configured in other ways such as serving as an adapter for connecting various accessories usable in a neurosurgical procedure, i.e. a navigation reference element, a retractor, etc. In view of the teachings herein, various other configurations for adapters to couple with lateral portions (120, 1120, 2120) will be apparent to those of ordinary skill in the art.

VI. Exemplary Alternative Adapter and Lateral Portion Tubular Member

Figure 11:
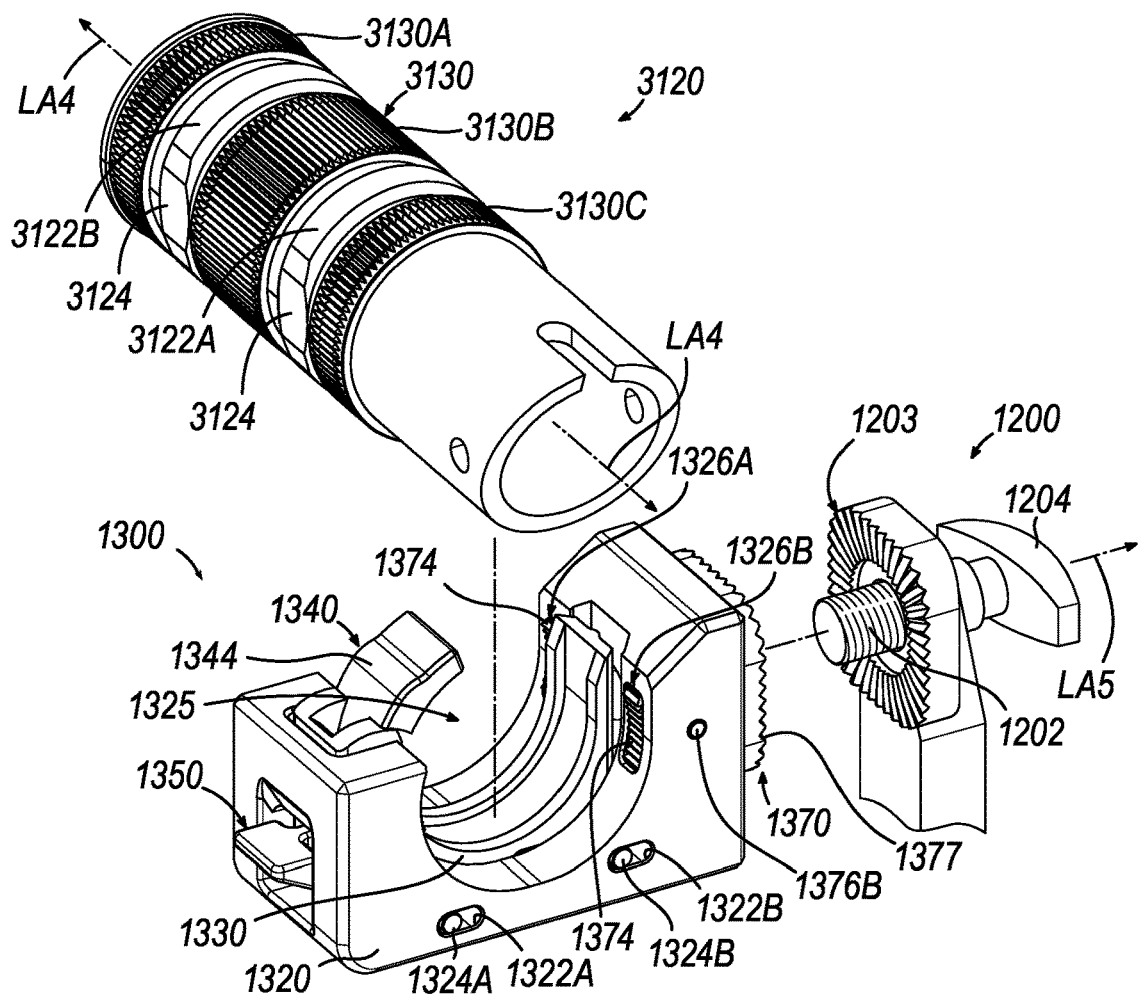
FIG. 11 depicts an exploded perspective view of another exemplary adapter, a tubular member of a lateral or base portion of a head stabilization device, and joint assembly, usable as components of a head stabilization system the same or similar to that shown in FIG. 1.

FIG. 11 illustrates another exemplary adapter (1300) that is usable in a head stabilization system and with a head stabilization device, such as head stabilization device (100). In some instances, adapter (1300) is useable with a version of head stabilization device (100) where lateral or base portion (120) is fitted with tubular member (3120), which is depicted in FIG. 11, to replace the tubular portion having engaging members (130) of lateral portion (120) as shown in FIG. 1. Tubular member (3120), in the present example, is a hollow structure in the form of a tube or hollow cylinder. In the present example, lateral portion (120) comprises multiple—in the illustrated version, two—telescopic tubular members where each are hollow and one is received by the other. With this configuration, lateral portion or base (120) of head stabilization device (100) comprises a hollow or substantially hollow structure, and with telescopic components so as to adjust a width dimension of head stabilization device (100). Furthermore, lateral portion or base (120) fitted with tubular member (3120) defines a longitudinal axis (LA4), which coincides with longitudinal axis (LA1) shown in FIG. 1.

Figure 12:
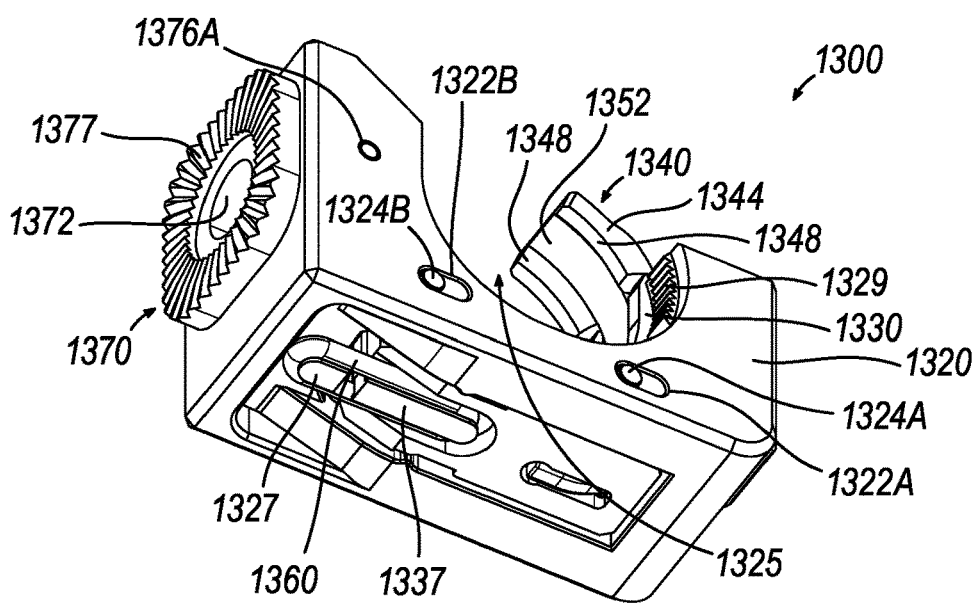
FIG. 12 depicts a bottom perspective view of the adapter of FIG. 11.

Referring to FIGS. 11 and 12, adapter (1300) includes locking member (1370) at its distal end such that adapter (1300) is configured to connect with another structure of the head stabilization system via locking member (1370). For instance, in some head stabilization systems, a joint assembly (1200), as shown in FIG. 11, is connectable with locking member (1370) of adapter (1300) via engagement of a threaded rod (1202) and a corresponding threaded bore (1372), and engagement of corresponding geared or starburst interfaces (1377, 1203). In the present example, this engagement is accomplished by turning actuation member or knob (1204). As will be understood by those of ordinary skill in the art, joint assembly (1200) further is connectable with a base unit (not shown), and the base unit is connectable with a patient support table or operating table (not shown). In some instances, joint assembly (1200) comprises or may be referred to as a swivel adapter. In other instances, joint assembly (1200) comprises one or more components other than, or in addition to, a swivel adapter. Furthermore, joint assembly (1200) defines a longitudinal axis (LA5) that is orthogonal to the longitudinal axis defined by lateral portion or base (120) fitted with tubular member (3120). With this arrangement, adapter (1300) is rotationally adjustable about longitudinal axis (LA5).

Locking member (1370) includes engaging members (1374) opposite to starburst interface (1377). As will be discussed in greater detail below, engaging members (1374) are each configured to selectively engage with engaging members of tubular member (3120), that in the present example are in the form of a gear ring or plurality of teeth (3130). As shown in the present example, tubular member (3130) includes multiple regions of pluralities of teeth, e.g., a first region of a plurality of teeth (3130A), a second region of a plurality of teeth (3130B), and a third region of a plurality of teeth (3130C). These regions are separated by raised portions (3122A, 3122B). As shown, each region of plurality of teeth (3130A, 3130B, 3130C) are configured in a radial manner such that they extend about an outer circumference of tubular member (3120).

In addition to locking member (1370), adapter (1300) includes an attachment support (1320), a slide support (1330), and a snap element (1340). Attachment support (1320) includes a pair of elongated slots (1322A, 1322B) that extend from one side to the other. Residing within slots (1322A, 1322B) are pins (1324A, 1324B) that extend through slots (1322A, 1322B) and further connect and extend through slide support (1330) via bores in slide support (1330). Pin (1324A) further connects and extends through an actuator member (1350) of snap element (1340) via a bore. In the present example, actuator member (1350) is in the form of a lever.

Figure 17:
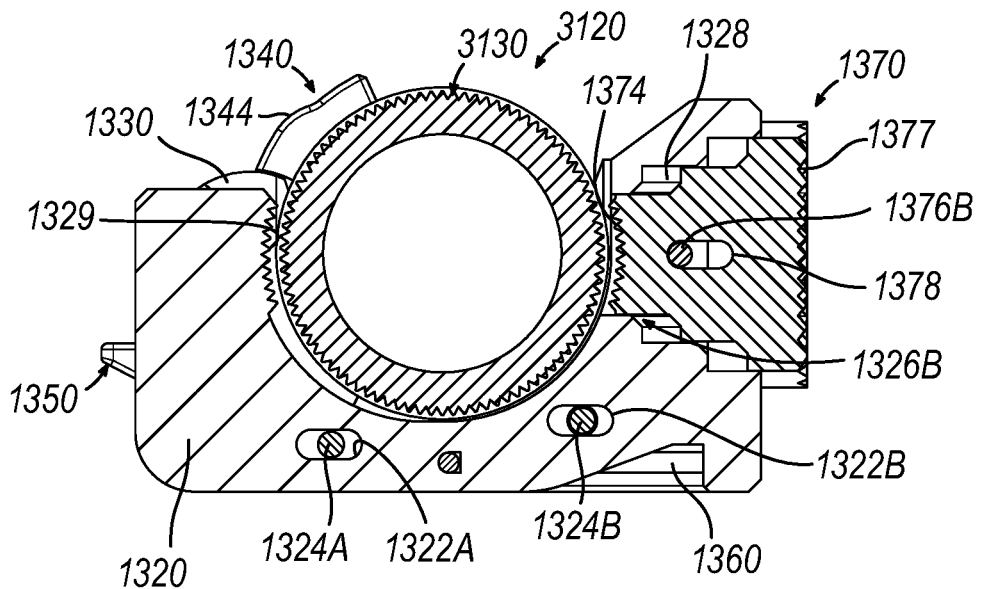
FIG. 17 depicts another cross-section view of FIG. 15.

Attachment support (1320) further includes a pair of elongated bores (1326A, 1326B) that connect with a distal recess (1328) shown in FIG. 17. Locking member (1370) is configured to fit within distal recess (1328) with engaging members (1374) extending within elongated bores (1326A, 1326B). Furthermore, locking member (1370) is configured to translate laterally within distal recess (1328), which thereby changes the relative position between locking member (1370) and attachment support (1320). In this manner, locking member (1370) is connected with attachment support (1320) by a pinned connection via pins (1376A, 1376B) on each side of locking member (1370). To permit translation of locking member (1370) relative to attachment support (1320), pins (1376A, 1376B) are received by an elongated slot (1378) on each side of locking member (1370) as shown in FIG. 17.

Figure 13:
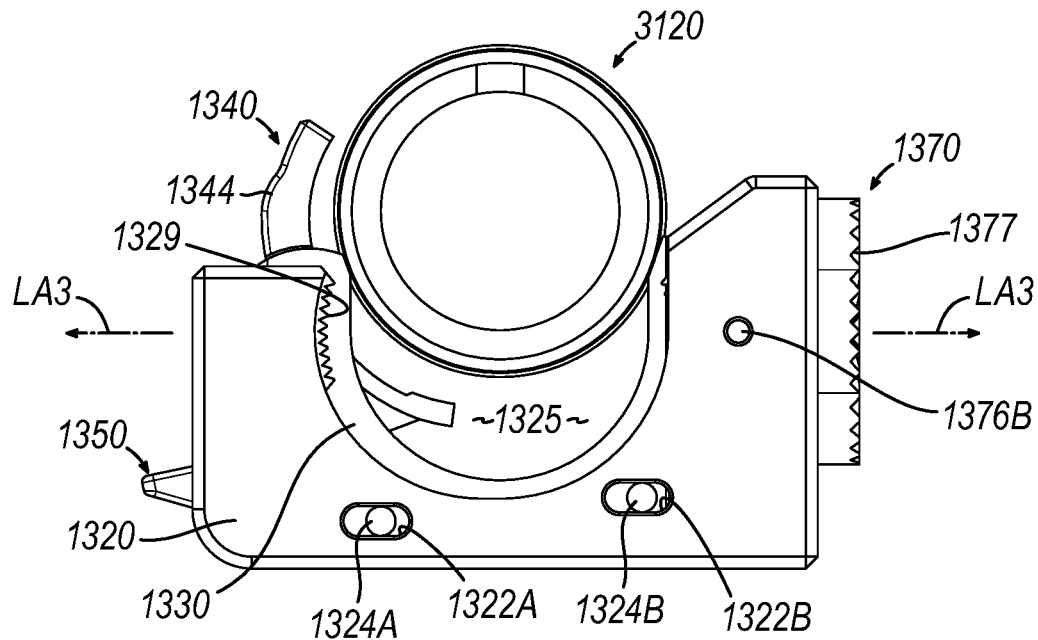
FIG. 13 depicts a front view of the adapter of FIG. 11, shown with an exemplary snap element rotated to an open position and with the tubular member partially within a space defined by the adapter.

Slide support (1330) is located within a cylindrical shaped void or space (1325) of attachment support (1320), and as mentioned has a pinned connection with attachment support (1320). Slide support (1330) has a curved shape thereby contributing to defining cylindrical shaped void or space (1325). Because of the configuration of elongated bores (1322A, 1322B) and the pinned connection between slide support (1330) and attachment support (1320), slide support (1330) is translatable relative to attachment support (1320) along longitudinal axis (LA3) as shown in FIG. 13, which coincides with longitudinal axis (LA2) of FIG. 1. This translational movement will be described in greater detail below.

Connected with slide support (1330) is snap element (1340). With this connection, snap element (1340) moves in unison with slide support (1330) when slide support (1330) translates. Snap element (1340) includes actuator member (1350) in the form of a lever in the present example. Snap element (1340) further includes an arm (1344). In the present example, pin (1324A) extends through a bore in actuator member (1350), and thereby actuator member (1350) has a pinned connection with slide support (1330), as well as with attachment support (1320). Actuator member (1350) is further rotatable about pin (1324A). With its rotatability, actuator member (1350) is selectively engageable with arm (1344) as will be described further below.

Figure 14:
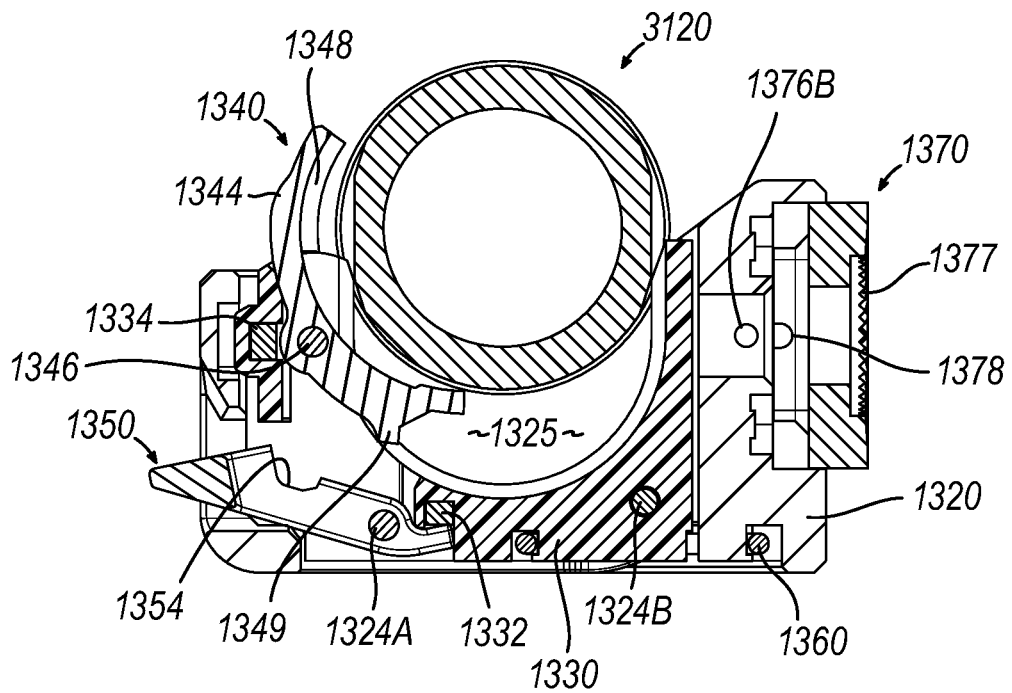
FIG. 14 depicts a cross-section view of FIG. 13.

Arm (1344) has a pinned connection with slide support (1330) as seen in FIG. 14 by pin (1346). Arm (1344) is rotatable about pin (1346) as will be discussed further below. In the present example, arm (1344) comprises a curved shape that complements an outer surface of tubular member (3120). More specifically, in the present version, arm (1344) comprises a pair of outer rails (1348) with a curved surface (1352) between outer rails (1348). In the present example, tubular member (3120) includes an outer surface portion that complements the rails (1348) and curved surface (1352) of arm (1344). For instance, tubular member (3120) includes raised portions (3122A, 3122B) configured to fit within curved surface (1352) of arm (1344) between rails (1348). In this manner snap element (1340) is configured to selectively engage with tubular member (3120) as will be discussed further below.

FIG. 12 illustrates an underside portion of adapter (1300) along with the distal end having interface (1377) and threaded bore (1372). As also seen in FIG. 12, attachment support (1320) includes engaging members (1329) on each side. In the present example, engaging members (1329) are fixed relative to attachment support (1320). Attachment support (1320) and slide support (1330) each include hook members (1327, 1337). Furthermore, adapter (1300) includes a fastener (1360) that connects attachment support (1320) and slide support (1330) about their respective hook members (1327, 1337). In the present example, fastener (1360) comprises an O-ring that is elastomeric such that it can expand and contract based on the relative positions of attachment support (1320) and slide support (1330). For instance, when tubular member (3120) is separate from adapter (1300) as shown in FIG. 11, fastener (1360) is contracted such that it pulls slide support (1330) distally relative to attachment support (1320). As will be discussed further below, when tubular member (3120) is located within adapter (1300), and when locking member (1370) is advanced proximally, slide support (1330) is pushed proximally and in response thereto fastener (1360) expands to permit this movement of slide support (1330).

FIGS. 13 through 19 illustrate views of adapter (1300) and tubular member (3120) showing a series where tubular member (3120) is installed with adapter (1300) and moved from an adjustable state to a locked or fixed state. FIGS. 13 and 14 illustrate tubular member (3120) partially inserted within adapter (1300). As shown, locking member (1370) is translated distally to make space to accommodate tubular member (3120). In operation, joint assembly (1200) is loosened which then allows locking member (1370) to translate distally away from snap element (1340). Slide support (1330) is moved distally as well as fastener (1360) is biased to a size that pulls slide support (1330) distally in the absence of a counteracting force. Moving distally with slide support (1330) is snap element (1340).

To install or insert tubular member (3120) with or into adapter (1300), actuator member (1350) is depressed, which disengages actuator member (1350) from arm (1344) of snap element (1340). Thereafter, arm (1344) is free to rotate about pin (1346) and does so as tubular member (3120) enters cylindrical shaped space or void (1325). To ensure proper alignment of tubular member (3120) with adapter (1300), tubular member (3120) is oriented such that when inserting tubular member (3120) within adapter (1300), arm (1344) aligns with one of raised portions (3122A, 3122B). Once tubular member (3120) is inserted within adapter over halfway, arm (1344) begins to rotate distally cradling tubular member (3120).

Adapter (1300) also includes resilient members (1332, 1334) positioned within slide support (1330). As seen in FIG. 14, resilient member (1332) contacts actuator member (1350) and slide support (1330). When depressing actuator member (1350), resilient member (1332) is compressed to allow actuator member (1350) to rotate away from arm (1344). When actuator member (1350) is no longer depressed, the natural bias of resilient member (1332) pushes on actuator member (1350) to cause actuator member (1350) to rotate back to the position shown in FIG. 11. Resilient member (1334) contacts arm (1344) and slide support (1330). When arm (1344) rotates proximally, resilient member (1334) is compressed to allow arm (1344) to rotate away from tubular member (3120). As tubular member (3120) is more fully inserted within adapter (1300), the natural bias of resilient member (1344) pushes on arm (1344) to cause arm (1344) to rotate distally back towards the position shown in FIG. 11. In some versions resilient members (1332, 1334) are elastomeric members, while in other versions they may be a springs or similar structures.

Figure 15:
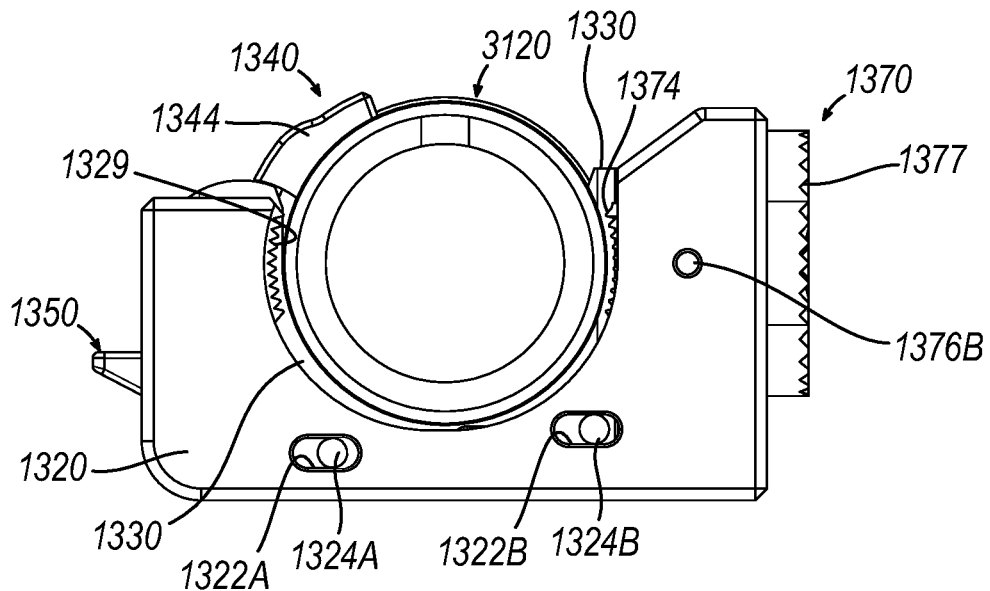
FIG. 15 depicts a front view of the adapter and the tubular member of FIG. 11, showing the tubular member fully seated within the space defined by the adapter, and further shown with the adapter in an open or adjustable position allowing rotatable adjustability of the tubular member.
Figure 16:
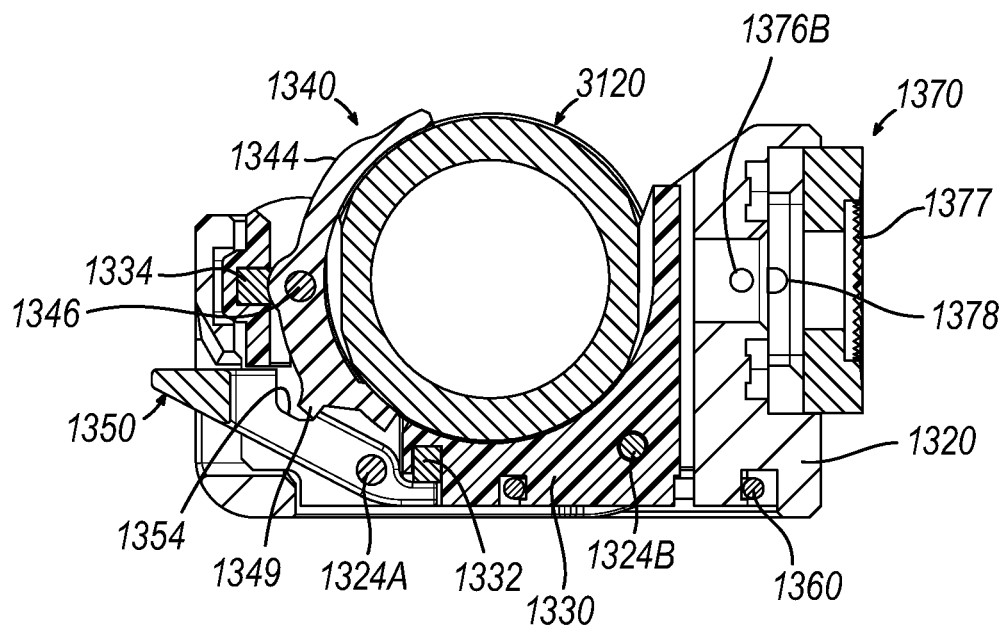
FIG. 16 depicts a cross-section view of FIG. 15.

FIGS. 15-17 show tubular member (3120) fully seated or positioned within adapter (1300) and in an adjustable state with engaging members (1329, 1374) disengaged from the gear rings or plurality of teeth (3130) of tubular member (3120) as shown in FIG. 17. In this configuration, locking member (1370) remains translated distally away from tubular member (3120). Similarly, slide support (1330) remains translated distally away from engaging members (1329). Therefore, tubular member (3120) can be adjusted rotationally, and because it is a component of head stabilization device (100) such rotation will rotate head stabilization device (100) about longitudinal axis (LA4) defined by tubular member (3120), which coincides with longitudinal axis (LA1) shown in FIG. 1.

In the present example with tubular member (3120), a preferred lateral position of tubular member (3120) relative to adapter (1300) can be selected prior to installing tubular member (3120) with adapter (1300). This is done by choosing which raised portion (3122A, 3122B) to align with snap element (1344). In some other versions, tubular member (3120) may be modified or replaced with another tubular member without these raised portions (3122A, 3122B). For example, such modifications may be similar to using tubular members like those of lateral portions (120, 1120, 2120) described above. In these and other instances, it is possible that the lateral position of the tubular member, and thus head stabilization device (100) can be adjusted with the tubular member fully seated within adapter (1300).

As shown in FIGS. 15-17, with tubular member (3120) fully seated within adapter (1300), arm (1344) rotates distally as well as actuator member (1350), and they engage one another in an interference fit. More specifically, arm (1344) includes projection (1349), which engages with notch (1354) in actuator member (1350). In this manner, snap element (1340) is in a locked state such that arm (1344) cannot rotate away from tubular member (3120) unless actuator member (1350) is depressed to disengage projection (1349) from notch (1354). This configuration ensures retention of tubular member (3120) with adapter (1300) when adapter (1300) is in the adjustable state that permits rotational adjustment of tubular member (3120) and hence head stabilization device (100). The complementing shapes of raised portions (3122A, 3122B) and curved surface (1352) of arm (1344) allow for contact yet sliding movement such that the engagement of arm (1344) with tubular member (3120) does not prevent tubular member (3120) from being rotatably adjusted.

Figure 18:
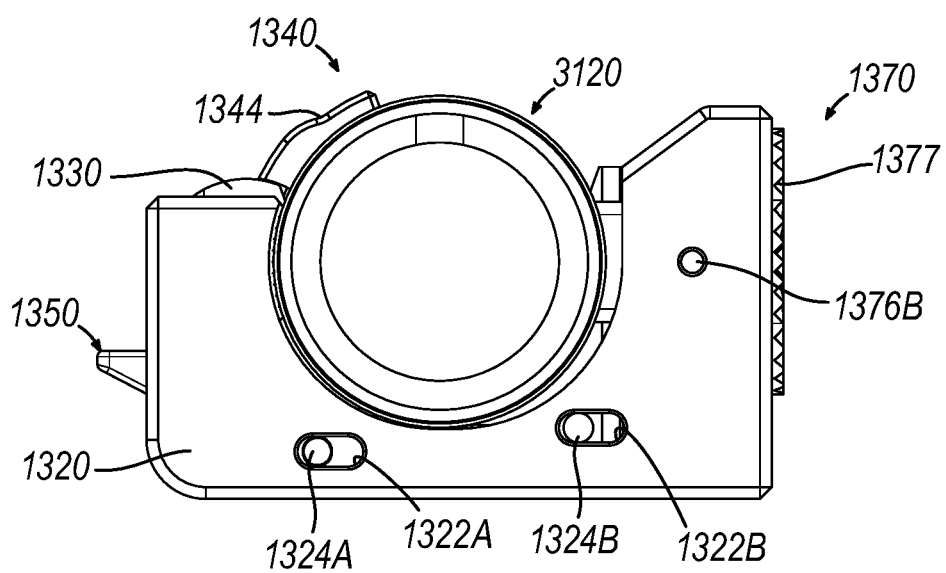
FIG. 18 depicts a front view of the adapter and the tubular member of FIG. 11, showing the tubular member fully seated within the space defined by the adapter, and further shown with the adapter in an closed or locked position fixing the rotatable position of the tubular member relative to the adapter.
Figure 19:
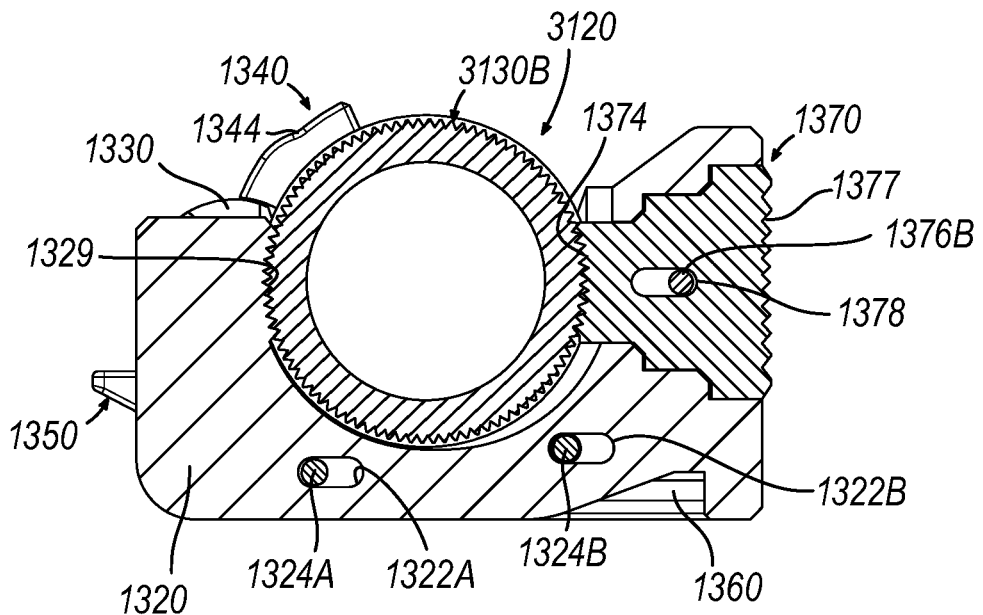
FIG. 19 depicts a cross-section view of FIG. 18.

FIGS. 18 and 19 depict views of adapter (1300) with tubular member (3120) fully installed with adapter (1300) and in the locked or fixed state where tubular member (3120) is rotationally fixed relative to adapter (1300). In the illustration version with this configuration, one of engaging members (1374) contacts and engages with first region of plurality of teeth (3130A) and the other of engaging members (1374) contacts and engages with second region of plurality of teeth (3130B). This engagement occurs in response to locking member (1370) translating proximally toward snap element (1340). As stated earlier, the translation of locking member (1370) occurs in response to tightening joint assembly (1200), which engages joint assembly (1200) with locking member (1370).

As also seen in FIG. 19, in this locked state, first and second regions of plurality of teeth (3130A, 3130B) engage with engaging member (1329) of attachment support (1320). To accomplish this engagement, as locking member (1370) is tightened and translated proximally toward snap element (1340), locking member (1370) contacts tubular member (3120) causing tubular member (3120) and slide support (1330) to translate proximally until tubular member (3120) contacts engaging members (1329) of attachment support (1320). Due to the force imparted by locking member (1370) on tubular member (3120) and slide support (1330), as slide support (1330) translates proximally, fastener (1360) elastically deforms and increases in length to allow slide support (1330) to move relative to attachment support (1320).

VII. Exemplary Alternative Adapter with Stops

Figure 20:
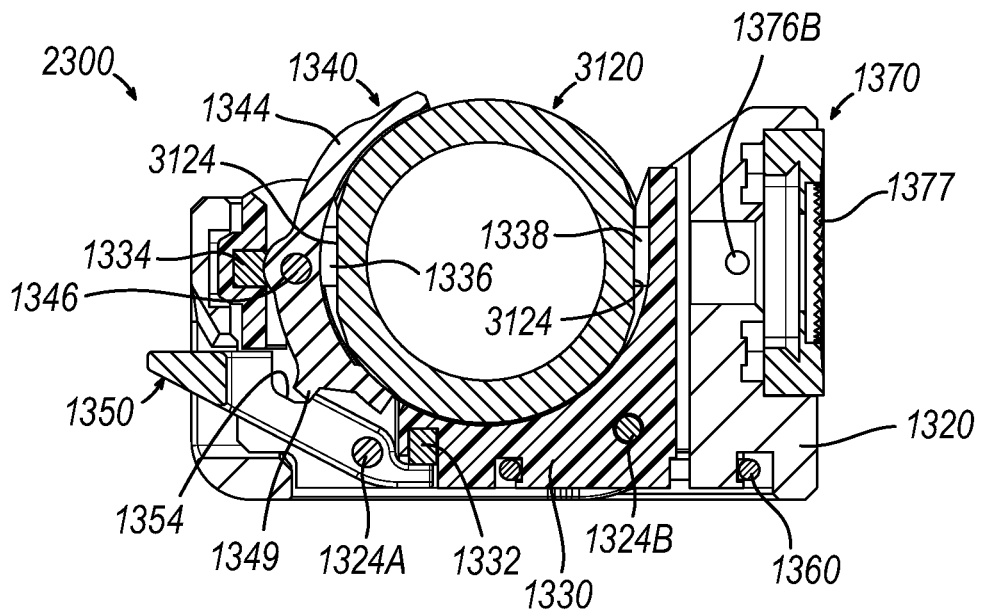
FIG. 20 depicts a cross-section view of another exemplary adapter the same as that shown in FIG. 18 but further including stops that prevent rotation of the tubular member within the adapter.

In some instances, it may be desirable to limit or prohibit rotation of tubular member (3120) when installed with adapter (1300). In such instances, a modified adapter, or adapter (2300), can be used as shown in FIG. 20. Adapter (2300) is identical with adapter (1300) described above except for the addition of stop members (1336, 1338), which are discussed below. The remaining structures and operation of adapter (2300) are identical with adapter (1300) discussed above, it being understood that the above discussion of adapter (1300) applies here to adapter (2300) with the exception of the rotational adjustment aspects of tubular member (3120) discussed below.

With adapter (2300), slide support (1330) includes stop (1338), with stop (1338) mounted on the distal side of slide support (1330) opposite to snap element (1340). Similarly, stop (1336) is mounted on arm (1344) along curved surface (1352). Also referring back to FIG. 11, tubular member (3120) includes flat surfaces (3124) that are arranged on opposite sides of tubular member (3120) in two locations. In operation, stops (1336, 1338) contact flat surfaces (3124) on each side of tubular member (3120) during the installation of tubular member (3120) with adapter (2300) and remain in contact when tubular member (3120) is fully seated or installed within adapter (2300). In this manner, tubular member (3120) is not rotatably adjustable when installed with adapter (2300). Furthermore, tubular member (3120) incorporates features that both allow tubular member (3120) to be used with adapters configured to allow rotatable adjustability, like adapter (1300), and to be used with adapters configured to prohibit rotatable adjustability, like adapter (2300). Of course this is not required in all versions and in some instances tubular members can be modified to be specific to a particular style of adapter. In view of the teachings herein, those of ordinary skill in the art will appreciate various ways to modify tubular members and adapters to permit or restrict rotation adjustability.

VIII. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A device for stabilizing or supporting a head of a patient during a medical procedure comprises a base having a plurality of engaging members on an outer surface of the base and extending around the base.

Example 2

The device of Example 1, comprising a skull clamp, wherein the base defines a lateral portion of the skull clamp.

Example 3

The device of Example 2, wherein the skull clamp comprises a pair of upright portions, wherein the base defining the lateral portion extends between the pair of upright portions.

Example 4

The device of Example 3, wherein each one of the pair of upright portions is configured to retain a stabilization assembly having one or more pins configured to contact the head of the patient.

Example 5

The device of any one or more of Example 1 through Example 4, wherein the base is cylindrically shaped, and the plurality of engaging members extend around the circumference of the outer surface of the base.

Example 6

The device of any one or more of Example 1 through Example 5, wherein the plurality of engaging members comprises a plurality of teeth.

Example 7

The device of any one or more of Example 1 through Example 5, wherein the plurality of engaging members comprises a gear ring extending continuously around the base.

Example 8

The device of any one or more of Example 1 through Example 7, wherein the plurality of engaging members is oriented radially about the outer surface of the base.

Example 9

The device of any one or more of Example 1 through Example 8, wherein the plurality of engaging members is configured to engage with an adapter, and wherein the base defining the lateral portion defines a first longitudinal axis.

Example 10

The device of Example 9, wherein the device is rotationally adjustable about the first longitudinal axis relative to the adapter.

Example 11

The device of any one or more of Example 9 through Example 10, wherein the device is laterally adjustable along the first longitudinal axis relative to the adapter.

Example 12

The device of any or more of Example 9 through Example 11, wherein the adapter is configured to engage with a joint assembly, wherein the joint assembly defines a second longitudinal axis that is orthogonal to the first longitudinal axis defined by the lateral portion, wherein the device is rotationally adjustable about the second longitudinal axis.

Example 13

The device of any one or more of Example 1 through Example 12, wherein the plurality of engaging members is sized and configured to receive two or more adapters.

Example 14

The device of any one or more of Example 1 through Example 12, comprising two or more pluralities of engaging members, wherein the pluralities of engaging members are spaced apart from one another along the base.

Example 15

The device of Example 14, wherein the two or more pluralities of engaging members are each configured to engage with two or more adapters, with each of the pluralities of engaging members engaging one of the two or more adapters.

Example 16

The device of any one or more of Example 14 through Example 15, wherein at least one of the pluralities of engaging members is sized and configured to receive two or more adapters.

Example 17

A device for stabilizing a patient comprises a head stabilization device having a frame that defines a lateral portion, wherein the lateral portion defines a first longitudinal axis. The device further comprises a joint assembly defining a second longitudinal axis orthogonal to the first longitudinal axis, wherein the joint assembly comprises an adapter and a proximal joint, wherein at least a portion of the adapter is translatable and rotatable relative to the proximal joint. The head fixation device is connectable with the adapter such that the head fixation device is rotatable about the first and second longitudinal axes. The joint assembly is configured to move between an open state and closed state, wherein the joint assembly, in the open state, allows rotation of the head stabilization device about the first and second longitudinal axes. The joint assembly, in the closed state, inhibits rotation of the head stabilization device about the first and second longitudinal axes.

Example 18

The device of Example 17, wherein the adapter comprises a first support and a second support, wherein the first support is slidingly received within the second support, wherein the first support is movable relative to the second support to receive the head stabilization device within a space defined by the first and second supports.

Example 19

The device of Example 18, wherein each of the first and second supports comprises a plurality of engaging members that are configured to selectively engage a plurality of engaging members of the head stabilization device.

Example 20

The device of any one or more of Example 18 through Example 19, wherein the first support is resiliently biased away from the second support.

Example 21

The device of any one or more of Example 17 through Example 20, wherein the adapter comprises a snap element that is resiliently biased toward an interior surface of the adapter, wherein the snap element is translatable within the adapter when the head stabilization device is inserted within the adapter such that the snap portion is configured to maintain the head stabilization device within the adapter.

Example 22

The device of Example 21, wherein the snap element comprises a beveled surface.

Example 23

The device of any one or more of Example 17 through Example 22, wherein the joint assembly comprises a first locking feature coupled with the adapter, wherein the first locking feature is movable between a first and second position such that the first locking feature is configured to actuate the joint assembly between the open and closed states when the first locking feature is moved between the first and second positions.

Example 24

The device of Example 23, wherein the first locking feature comprises a lever that is pivotable relative to the adapter, wherein pivoting the lever translates the adapter relative to the proximal joint.

Example 25

The device of Example 23, wherein the joint assembly comprises a second locking feature coupled with the adapter, wherein the second locking feature is selectively coupled with the first locking feature such that the second locking feature is configured to maintain the first locking feature in the second position to thereby maintain the joint assembly in the closed state.

Example 26

The device of Example 25, wherein the second locking feature comprises a bar that is translatable relative to the first locking feature.

Example 27

The device of Example 23, wherein the joint assembly comprises a second locking feature connectable with the adapter, wherein the first locking feature is configured to actuate the second locking feature to selectively engage with the proximal joint to inhibit the adapter from rotating relative to the proximal joint.

Example 28

The device of Example 27, wherein the second locking feature comprises a shaft translatable relative to the proximal joint, wherein the second locking feature includes a plurality of engaging members configured to selectively engage a plurality of engaging members of the proximal joint.

Example 29

The device of any one or more of Example 17 through Example 28, wherein the adapter includes a channel for receiving a flange of the proximal joint, wherein the flange of the proximal joint defines an annular recess about the flange, wherein at least one pin is inserted within the channel of the adapter and within the annular recess of the proximal joint to allow the adapter to rotate relative to the proximal joint.

Example 30

The device of any one or more of Example 17 through Example 29, wherein the head stabilization device comprises a skull clamp, wherein the lateral portion comprises an outer surface and one or more sets of a plurality of engaging members oriented radially about the outer surface of the lateral portion.

Example 31

A joint assembly connectable with a head stabilization device for stabilizing a patient, comprises an adapter including a first support, and a second support coupled with the first support such that the first support is translatable relative to the second support. The adapter is configured to receive the head stabilization device within a space defined by the first and second supports. The joint assembly further comprises a proximal joint, wherein the adapter is rotatable relative to the proximal joint about a longitudinal axis of the joint assembly. The joint assembly further comprises a first locking feature coupled with the adapter, wherein the first locking feature is selectively movable from a first position to a second position to actuate the joint assembly from an open state to a closed state. The first position of the first locking feature corresponds to the open state of the joint assembly such that the first support is spaced a distance away from the second support. The first locking feature is configured to move to the second position to actuate the joint assembly to the closed state by translating the first support toward the second support.

Example 32

The joint assembly of Example 31, wherein the head stabilization device is rotatable about a first longitudinal axis defined by the head stabilization device and a second longitudinal axis defined by the joint assembly when the joint assembly is in the open state. The joint assembly is further configured to inhibit the rotation of the head stabilization device about the first and second longitudinal axes when the joint assembly is in the closed state.

Example 33

The joint assembly of any one or more of Example 31 through Example 32, wherein each of the first and second supports comprise a plurality of engaging members positioned on an interior surface of each of the first and second supports that are configured to engage a plurality of engaging members of the head stabilization device in the closed state.

Example 34

The joint assembly of any one or more of Example 31 through Example 33, further comprising a second locking feature selectively couplable with the first locking feature such that the second locking feature is configured to maintain the first locking feature in the second position to thereby maintain the joint assembly in the closed state.

Example 35

The joint assembly of any one or more of Example 31 through Example 33, further comprising a second locking feature positioned between the adapter and proximal joint, wherein the first locking feature is configured to actuate the second locking feature to selectively engage with the proximal joint to inhibit the adapter from rotating relative to the proximal joint.

Example 36

A method of operating a device for stabilizing a patient, wherein the device comprises a head stabilization device defining a first longitudinal axis, a joint assembly defining a second longitudinal axis orthogonal relative to the first longitudinal axis, wherein the joint assembly comprises an adapter translatable and rotatable relative to a proximal joint of the joint assembly. The method comprises the steps of: (a) inserting the head fixation device into the adapter; (b) rotating the head fixation device about a select one or both of the first and second longitudinal axes to adjust the position of the head fixation device; (c) actuating the joint assembly from an open state to a closed state to inhibit rotation of the head stabilization device about the first and second longitudinal axes; and (d) actuating the joint assembly from the closed state to the open state to thereby allow the head stabilization device to rotate about a select one or both of the first and second longitudinal axes.

Example 37

A device for stabilizing a patient comprises a positioning assembly defining a first longitudinal axis. The positioning assembly comprises an interior space and one or more sets of a plurality of engaging members within the interior space. The positioning assembly is configured to move between an adjustable state and locked state. The device further comprises a skull clamp having a pair of upright portions and a lateral portion extending between the pair of upright portions. The lateral portion comprises an outer surface and one or more sets of a plurality of engaging members oriented radially about the outer surface of the lateral portion. The lateral portion defines a second longitudinal axis, and the skull clamp is connectable with the positioning assembly by locating the lateral portion within the interior space of the positioning assembly such that the one or more sets of the plurality of engaging members of the positioning assembly are selectively engageable with the one or more sets of the plurality of engaging members of the lateral portion of the skull clamp. In the adjustable state the skull clamp is rotatable about the first and second longitudinal axes, and in the locked state the skull clamp is fixed relative to the first and second longitudinal axes.

Example 38

The device of any one or more of Example 1 through Example 16, wherein the base is hollow.

Example 39

The device of any one or more of Example 1 through Example 16, or of Example 38, wherein the base comprises multiple members that are telescopically adjustable relative to one another.

Example 40

The device of Example 1, the device comprising a skull clamp, wherein the base defines a lateral portion of the skull clamp, wherein the skull clamp comprises a pair of upright portions, wherein the base defining the lateral portion extends between the pair of upright portions, wherein each one of the pair of upright portions is configured to retain a stabilization assembly having one or more pins configured to contact the head of the patient.

Example 41

The device of any one or more of Example 1 and Example 40, wherein the base is cylindrically shaped, and the plurality of engaging members extend around the circumference of the outer surface of the base.

Example 42

The device of any one or more of Example 1 and Example 40 through Example 41, wherein the plurality of engaging members comprises a gear ring extending continuously around the base.

Example 43

The device of any one or more of Example 1 and Example 40 through Example 42, wherein the plurality of engaging members is oriented radially about the outer surface of the base.

Example 44

The device of any one or more of Example 1 and Example 40 through Example 43, wherein the plurality of engaging members is configured to engage with an adapter, and wherein the base defining the lateral portion defines a first longitudinal axis, wherein the device is rotationally adjustable about the first longitudinal axis relative to the adapter.

Example 45

The device of Example 44, wherein the device is laterally adjustable along the first longitudinal axis relative to the adapter.

Example 46

The device of any one or more of Example 44 through Example 45, wherein the adapter is configured to engage with a joint assembly, wherein the joint assembly defines a second longitudinal axis that is orthogonal to the first longitudinal axis defined by the lateral portion, wherein the device is rotationally adjustable about the second longitudinal axis.

Example 47

The device of any one or more of Example 1 and Example 40 through Example 46, the device comprising two or more pluralities of engaging members, wherein the pluralities of engaging members are spaced apart from one another along the base.

Example 48

The device of any one or more of Example 1 and Example 40 through Example 47, wherein the base is hollow.

Example 49

The device of any one or more of Example 1 and Example 40 through Example 48, wherein the base comprises multiple members that are telescopically adjustable relative to one another.

Example 50

A device for use with a head stabilization device having a frame that defines a lateral portion, wherein the lateral portion defines a first longitudinal axis and includes an outer surface and one or more sets of first engaging features oriented radially about the outer surface of the lateral portion, the device comprising second engaging features that are configured to selectively engage at least a portion of the first engaging features of the lateral portion of the head stabilization device permitting selective rotational adjustment of the head stabilization device about the first longitudinal axis.

Example 51

The device of Example 50, wherein the adapter comprises a first support and a second support, wherein the first support is movable relative to the second support to receive the head stabilization device within a space defined by the first and second supports.

Example 52

The device of any one or more of Example 50 through Example 51, wherein each of the first and second supports comprises a portion of the second engaging features that are configured to selectively engage the first engaging features of the head stabilization device.

Example 53

The device of any one or more of Example 50 through Example 52, the device comprising a snap element that is resiliently biased to maintain the lateral portion of the head stabilization device within the device once the lateral portion is received by the device.

Example 54

The device of Example 53, wherein the snap element comprises a complementing surface with a corresponding surface of the lateral portion that enables rotation of the lateral portion while the snap element maintains the lateral portion within the device.

Example 55

The device of any one or more of Example 50 through Example 54, the device comprising a locking member that is movable between a first and a second position such that the locking member is configured to selectively permit rotation of the head stabilization device when the locking member is moved between the first and second positions.

Example 56

The device of Example 55, wherein the locking member moves between the first and second positions in response to engagement with a joint assembly.

Example 57

A method of operating a device for stabilizing a patient, wherein the device comprises a head stabilization device defining a first longitudinal axis, a joint assembly defining a second longitudinal axis orthogonal relative to the first longitudinal axis, and an adapter connectable with the head stabilization device and the joint assembly and further rotatable relative to the joint assembly, the method comprising the steps of: (a) inserting the head fixation device into the adapter; (b) rotating the head fixation device about a select one or both of the first and second longitudinal axes to adjust the position of the head fixation device; and (c) actuating the joint assembly from an open state to a closed state to inhibit rotation of the head stabilization device about the first and second longitudinal axes.

Example 58

The method of Example 57, further comprising actuating the joint assembly from the closed state to the open state to thereby allow the head stabilization device to rotate about a select one or both of the first and second longitudinal axes.

Example 59

A device for stabilizing a head of a patient, the device comprising (a) an upright portion including a stabilization assembly configured to contact the head of the patient, and (b) a lateral portion that is round.

Example 60

The device of Example 59, wherein the device comprises a pair of upright portions, each having a stabilization assembly configured to contact the head of the patient, wherein the lateral portion extends between the pair of upright portions.

IX. Miscellaneous

The components described herein may be constructed of a variety of material that will be apparent to those of ordinary skill in the art in view of the teachings herein. In one version, all or some of the components are constructed of radiolucent materials so as to provide no or limited artifacts during various imaging modalities. In other versions, all or some of the components are constructed from nonradiolucent materials. Such materials may include aluminum or various metal alloys among other non-metal materials.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A device for stabilizing or supporting a head of a patient during a medical procedure, wherein the device comprises a skull clamp having a base defining a lateral portion of the skull clamp, wherein the base defines a first longitudinal axis and having a plurality of engaging members on an outer surface, wherein the plurality of engaging members extend about a circumference of the outer surface of the base and permit the selective rotational adjustment of the head stabilization device about the first longitudinal axis.

2. The device of claim 1 wherein the skull clamp comprises a pair of upright portions, wherein the base defining the lateral portion extends between the pair of upright portions, wherein each one of the pair of upright portions is configured to retain a stabilization assembly configured to contact the head of the patient.

3. The device of claim 1, wherein the base is cylindrically shaped.

4. The device of claim 1, wherein the plurality of engaging members comprises a gear ring extending continuously around the base.

5. The device of claim 1, wherein the plurality of engaging members is oriented radially about the outer surface of the base.

6. The device of claim 1, wherein the plurality of engaging members is configured to engage with an adapter, wherein the device is rotationally adjustable about the first longitudinal axis relative to the adapter.

7. The device of claim 6, wherein the device is laterally adjustable along the first longitudinal axis relative to the adapter.

8. The device of claim 6, wherein the adapter is configured to engage with a joint assembly, wherein the joint assembly defines a second longitudinal axis that is orthogonal to the first longitudinal axis, wherein the device is rotationally adjustable about the second longitudinal axis.

9. The device of claim 1, comprising two or more pluralities of engaging members, wherein the pluralities of engaging members are spaced apart from one another along the base.

10. The device of claim 1, wherein the base is hollow.

11. The device of claim 1, wherein the base comprises multiple members that are telescopically adjustable relative to one another.

12. A device for use with a head stabilization device having a frame that defines a lateral portion, wherein the lateral portion defines a first longitudinal axis and includes an outer surface and one or more sets of first engaging features oriented radially about the outer surface of the lateral portion, the device comprising second engaging features that are configured to selectively engage at least a portion of the first engaging features of the lateral portion of the head stabilization device permitting selective rotational adjustment of the head stabilization device about the first longitudinal axis and relative to the device.

13. The device of claim 12, wherein the device comprises a first support and a second support, wherein the first support is movable relative to the second support to receive the head stabilization device within a space defined by the first and second supports.

14. The device of claim 13, wherein each of the first and second supports comprises a portion of the second engaging features that are configured to selectively engage the first engaging features of the head stabilization device.

15. The device of claim 12, comprising a snap element that is resiliently biased to maintain the lateral portion of the head stabilization device within the device once the lateral portion is received by the device.

16. The device of claim 15, wherein the snap element comprises a complementing surface with a corresponding surface of the lateral portion that enables rotation of the lateral portion while the snap element maintains the lateral portion within the device.

17. The device of claim 12, comprising a locking member that is movable between a first and a second position such that the locking member is configured to selectively permit rotation of the head stabilization device when the locking member is moved between the first and second positions.

18. The device of claim 17, wherein the locking member moves between the first and second positions in response to engagement with a joint assembly.

19. A method of operating a device for stabilizing a patient, wherein the device comprises a head stabilization device defining a first longitudinal axis, a joint assembly defining a second longitudinal axis orthogonal relative to the first longitudinal axis, and an adapter connectable with the head stabilization device and the joint assembly and further rotatable relative to the joint assembly, the method comprising the steps of:
 (a) inserting the head stabilization device into the adapter;
  (b) rotating the head stabilization device, wherein the head stabilization device is capable of being rotated about the first and second longitudinal axes to adjust the position of the head stabilization device; and (c) actuating the joint assembly from an open state to a closed state to inhibit rotation of the head stabilization device about the first and second longitudinal axes.

20. The method of claim 19, further comprising actuating the joint assembly from the closed state to the open state to thereby allow the head stabilization device to rotate about a select one or both of the first and second longitudinal axes.

\* \* \* \* \*